(12) United States Patent
Ishihara et al.

(10) Patent No.: US 11,653,985 B2
(45) Date of Patent: May 23, 2023

(54) REMOTE CONTROL APPARATUS

(71) Applicant: MEDICAROID CORPORATION, Kobe (JP)

(72) Inventors: Kazuki Ishihara, Kobe (JP); Shiro Horita, Kobe (JP)

(73) Assignee: MEDICAROID CORPORATION, Kobe (JP)

( * ) Notice: Subject to any disclaimer, the term of this patent is extended or adjusted under 35 U.S.C. 154(b) by 800 days.

(21) Appl. No.: 16/001,057

(22) Filed: Jun. 6, 2018

(65) Prior Publication Data

US 2018/0353247 A1 Dec. 13, 2018

(30) Foreign Application Priority Data

Jun. 8, 2017 (JP) .............................. JP2017-113322

(51) Int. Cl.
*A61B 34/00* (2016.01)
*A61B 34/35* (2016.01)
(Continued)

(52) U.S. Cl.
CPC ............ *A61B 34/25* (2016.02); *A61B 1/0016* (2013.01); *A61B 1/00042* (2022.02); *A61B 1/045* (2013.01); *A61B 1/313* (2013.01); *A61B 34/35* (2016.02); *A61B 34/37* (2016.02); *A61B 34/70* (2016.02); *A61B 1/00045* (2013.01);
(Continued)

(58) Field of Classification Search
CPC ......... A61B 34/25; A61B 34/30; A61B 34/35; A61B 34/37; A61B 34/70; A61B 34/74; A61B 2034/301–303; A61B 1/00039; A61B 1/0016; A61B 34/32;
(Continued)

(56) References Cited

U.S. PATENT DOCUMENTS 5,883,615 A 3/1999 Fago et al.
5,889,510 A 3/1999 Klarlund
(Continued)

FOREIGN PATENT DOCUMENTS

CN 102421387 A 4/2012
CN 204695986 U 10/2015
(Continued)

*Primary Examiner* — Ryan N Henderson
*Assistant Examiner* — Pamela F Wu
(74) *Attorney, Agent, or Firm* — Metrolex IP Law Group, PLLC

(57) ABSTRACT

A remote control apparatus to remotely control a patient-side system including medical equipment and an endoscope to capture an image of a surgery site according to an embodiment includes: an operation handle with which an operator controls the medical equipment; and an operation pedal section. The operation pedal section includes: plural pedals configured to be pressed down to execute functions concerning the medial equipment; and a base on which the plural pedals are arranged, the plural pedals being arranged at locations not overlapping each other in a planar view. The plural pedals include first height pedals with upper ends thereof located at a first height position and second height pedals with upper ends thereof located at a second height position, which is different from the first height position. The first height pedals are arranged alternately with the second height pedals.

23 Claims, 15 Drawing Sheets

(51) Int. Cl.
*A61B 34/37* (2016.01)
*A61B 1/313* (2006.01)
*A61B 1/045* (2006.01)
*A61B 1/00* (2006.01)
*A61B 17/00* (2006.01)
*A61B 90/00* (2016.01)
*A61B 18/00* (2006.01)
*A61B 18/14* (2006.01)
*A61B 17/32* (2006.01)
*A61B 34/30* (2016.01)

(52) U.S. Cl.
CPC ... *A61B 17/320092* (2013.01); *A61B 18/1445* (2013.01); *A61B 34/74* (2016.02); *A61B 90/361* (2016.02); *A61B 90/37* (2016.02); *A61B 2017/00477* (2013.01); *A61B 2017/00973* (2013.01); *A61B 2018/00589* (2013.01); *A61B 2018/00601* (2013.01); *A61B 2034/302* (2016.02); *A61B 2034/742* (2016.02); *A61B 2090/371* (2016.02); *A61B 2090/372* (2016.02)

(58) Field of Classification Search
CPC ......... A61B 34/71–777; A61B 2034/731–733; A61B 90/361
USPC .... 600/102, 118, 126, 148; 378/189, 41–44; 606/46
See application file for complete search history.

(56) References Cited

U.S. PATENT DOCUMENTS

| | | | |
|---|---|---|---|
| 8,120,301 | B2 | 2/2012 | Goldberg et al. |
| 8,423,182 | B2 | 4/2013 | Robinson et al. |
| 9,271,806 | B2 | 3/2016 | Tran et al. |
| 9,301,811 | B2 | 4/2016 | Goldberg et al. |
| 2010/0225209 | A1 | 9/2010 | Goldberg et al. |
| 2010/0228264 | A1* | 9/2010 | Robinson ............... A61B 34/35 606/130 |
| 2013/0231681 | A1 | 9/2013 | Robinson et al. |
| 2015/0250439 | A1* | 9/2015 | Ishii ..................... A61B 6/54 378/115 |
| 2016/0066815 | A1* | 3/2016 | Mei ....................... B25J 9/1689 600/424 |
| 2018/0078034 | A1* | 3/2018 | Savall .................... A61B 90/60 |

FOREIGN PATENT DOCUMENTS

| | | |
|---|---|---|
| DE | 102004060240 A1 | 2/2006 |
| WO | 2008/098085 A2 | 8/2008 |
| WO | 2008/098085 A3 | 8/2008 |
| WO | 2009/114365 A2 | 9/2009 |
| WO | 2009/114365 A3 | 9/2009 |
| WO | 2009/114366 A2 | 9/2009 |
| WO | 2009/114366 A3 | 9/2009 |
| WO | 2016/077552 A1 | 5/2016 |

* cited by examiner

| F1: bipolar |
| F2: monopolar |
| F3: sealing device |

FIXED STATE

UNLOCK STATE

DETACH STATE

FIXED STATE

UNLOCK STATE

DETACH STATE

FIXED STATE

UNLOCK STATE

DETACH STATE

REMOTE CONTROL APPARATUS

CROSS REFERENCE TO RELATED APPLICATIONS

This application claims priority based on 35 USC 119 from prior Japanese Patent Applications No. 2017-113322 filed on Jun. 8, 2017, entitled "REMOTE CONTROL APPARATUS", the entire contents of which are incorporated herein by reference

BACKGROUND

The disclosure relates to a remote control apparatus and, more specifically, relates to a remote control apparatus to control medical equipment.

Surgical robots have been used in various surgeries such as laparoscopic surgery. As operating apparatuses for surgical robots, hand controllers and foot pedals have been used. With an increase in the functions of a surgical robot, the types of inputs from such a control apparatus increase, and an operator is required to efficiently operate such a control apparatus. A surgical robot of U.S. Pat. No. 8,120,301 (Patent Literature 1) uses foot pedals as a foot-side input section. The foot pedals are arranged in two height levels, including an upper pedal assembly and a lower pedal assembly, and accept inputs from many types of operations.

SUMMARY

In the control apparatus for the surgical robot described in Patent Literature 1, the foot pedals arranged in the two height levels require the operator to move his/her foot up and down. At operating a pedal in the upper level, the operator operates the upper pedal with the toe while keeping the toe and heel raised. In this case, the heel may accidentally touch and operate a pedal in the lower level.

An object of an embodiment is to provide a remote control apparatus improved in pedal operability while enabling a desirable number of types of input operations.

A first aspect of the disclosure is a remote control apparatus for remotely controlling a patient-side system including medical equipment and an endoscope to capture an image of a surgery site. The remote control apparatus includes: an operation handle with which an operator controls the medical equipment; and an operation pedal section.

The operation pedal section includes: plural pedals configured to be pressed down to execute functions concerning the medial equipment; and a base on which the plural pedals are arranged. The plural pedals are arranged at locations not overlapping each other in a planar view. The plural pedals include: first height pedals with upper ends thereof located at a first height position; and second height pedals with upper ends thereof located at a second height position, which is different from the first height position. The first height pedals are arranged alternately with the second height pedals.

A second aspect of the disclosure is a remote control apparatus for remotely controlling a patient-side system including medical equipment and an endoscope to capture an image of a surgery site. The remote control apparatus according to a second aspect includes: an operation handle with which an operator controls the medical equipment; and an operation pedal section including: plural pedals including first to fourth pedals configured to be pressed down to execute functions concerning the medial equipment; and a base on which the plural pedals are arranged. The first to fourth plural pedals are arranged at locations not overlapping each other in a planar view, such that the second pedal is provided adjacent to the first pedal, the third peal is provided adjacent to the second pedal, and the fourth pedal is provided adjacent to the third pedal. A position of upper ends of the first and third pedals are different from a position of upper ends of the second and fourth pedals in height.

A third aspect of the disclosure is a remote control apparatus for remotely controlling a patient-side system including a first manipulator supporting first medical equipment, a second manipulator supporting second medical equipment, and a camera arm supporting an endoscope. The remote control apparatus according to the third aspect includes: a first operation handle with which an operator operates the first medical equipment through the first manipulator; a second operation handle with which the operator operates the second medical equipment through the second manipulator; and an operation pedal section including: plural pedals including first to sixth pedals configured to be pressed down to execute functions concerning the first medical equipment, the second medical equipment, and the endoscope; and a base on which the plural pedals are arranged. The first to sixth plural pedals are arranged at locations not overlapping each other in a planar view, such that the second pedal is provided adjacent to the first pedal, the third peal is provided adjacent to the second pedal, the fourth pedal is provided adjacent to the third pedal, the fifth pedal is provided adjacent to the fourth pedal, and the sixth pedal is provided adjacent to the fifth pedal. A position of upper ends of the first, third, and fifth pedals are different from a position of upper ends of the second, fourth, and sixth pedals in height.

According to at least one of the aspects, it is possible to improve the pedal operability while enabling a desirable number of types of input operations.

DETAILED DESCRIPTION

Embodiments are explained with reference to drawings hereinafter.

First Embodiment

[Configuration of Remote Control Apparatus]

The configuration of a remote control apparatus 100 according to a first embodiment is described with reference to FIGS. 1 to 13.

Figure 1:
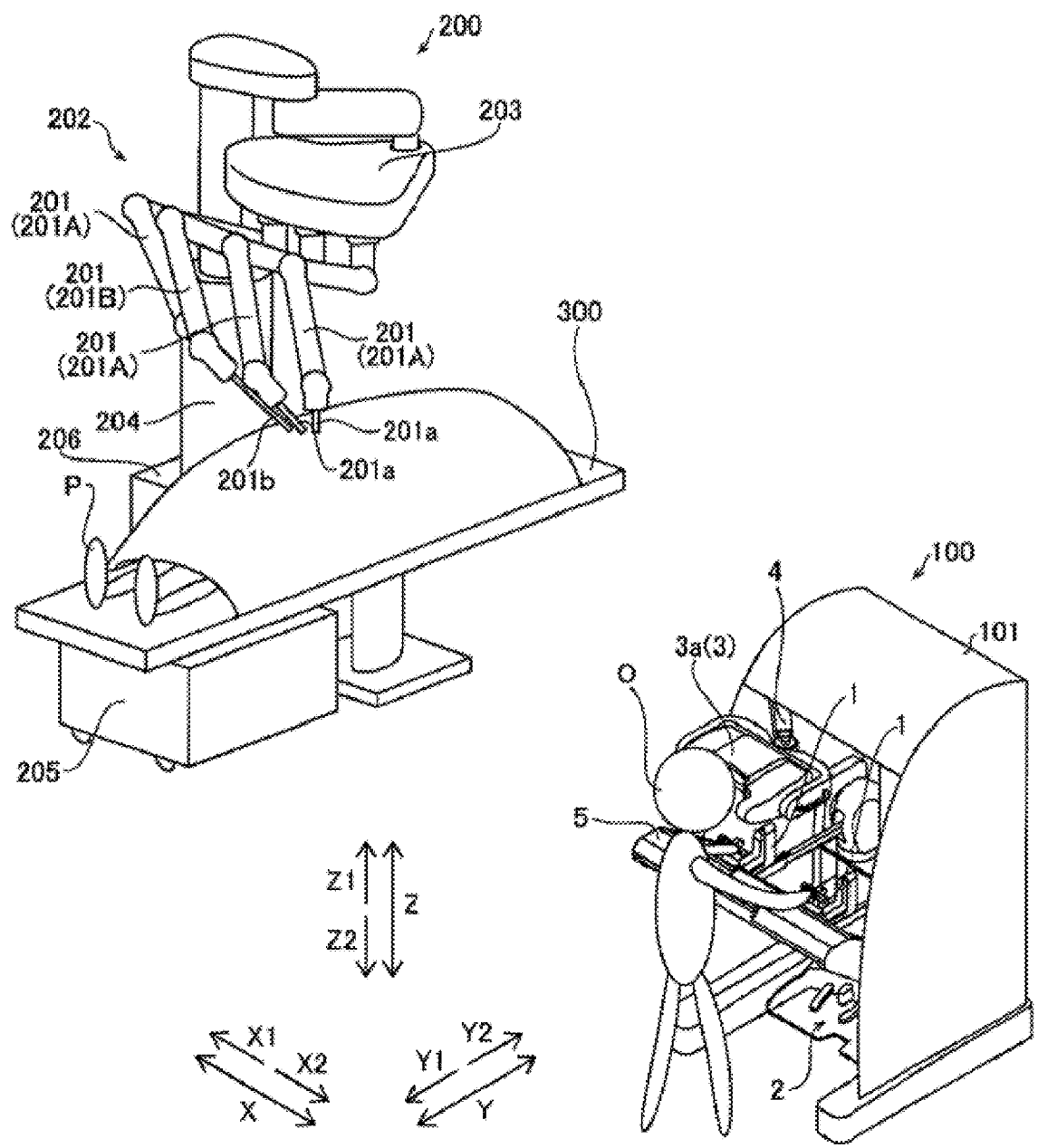
FIG. 1 is a schematic view illustrating a remote control apparatus according to a first embodiment.

As illustrated in FIG. 1, the remote control apparatus 100 is provided for teleoperation of medical equipment included in a patient-side system 200. When an operator O, as a surgeon, inputs an action mode instruction to be executed by the patient-side system 200, to the remote control apparatus 100, the remote control apparatus 100 transmits the action mode instruction to the patient-side system 200 through a controller 206. In response to the action mode instruction transmitted from the remote control apparatus 100, the patient-side system 200 operates medical equipment, such as surgical instruments and an endoscope, held by surgical manipulators 201. This allows for minimally invasive surgery. A surgery assisting system includes the remote control apparatus 100 and the patient-side system 200 including the surgical manipulators 201.

The patient-side system 200 constitutes an interface to perform a surgery for a patient P. The patient-side system 200 is placed beside an operation table 300 on which the patient P lies. The patient-side system 200 includes plural surgical manipulators 201. One of the surgical manipulators 201 holds an endoscope 201b while the others hold surgical instruments (instruments 201a). The surgical manipulator 201 holding surgical instruments (instruments 201a) function as instrument arms 201A while the surgical manipulator 201 holding the endoscope 201b functions as a camera arm 201B. The instrument arms 201A and camera arm 201B are commonly supported by a platform 203. Each of the surgical manipulators 201 includes plural joints. Each joint includes a driver including a servo-motor and a position detector such as an encoder. The surgical manipulators 201 are configured so that medical equipment attached to each surgical manipulator 201 is controlled by a driving signal given through the controller 206, to perform a desired movement.

The platform 203 is supported by a positioner 202 placed on the floor of an operation room. The positioner 202 includes a column 204 and a base 205. The column 204 includes an elevating shaft adjustable in the vertical direction. The base 205 includes wheels and is movable on the floor surface.

The instrument arms 201A detachably hold the instruments 201a as the medical equipment at the tips thereof. Each instrument 201a includes a housing and an end effector. The housing is attached to the instrument arm 201A. The end effector is provided at the tip of an elongated shaft. The end effector is grasping forceps, a hook, scissors, a high-frequency knife, a snare wire, a clamp, or a stapler, for example. The end effector is not limited to those and can be various types of treatment tools. In surgeries using the patient-side system 200, the instrument arms 201A are introduced into the body of the patient P through a cannula (trocar) placed on the body surface of the patient P, and the end effector of each instrument 201a is located near the surgery site.

To the tip of the camera arm 201B, the endoscope 201b (see FIG. 3), as the medical equipment, is detachably attached. The endoscope 201b captures an image within the body cavity of the patient P. The captured image is outputted to the remote control apparatus 100. The endoscope 201b is a 3D endoscope capable of capturing a three-dimensional image or a 2D endoscope. In surgeries using the patient-side system 200, the camera arm 201B is introduced into the body of the patient P through a trocar placed on the body surface of the patient P, and the endoscope 201b is located near the surgery site. The endoscope 201b is an example of an imaging section, or an imaging device.

The remote control apparatus 100 constitutes the interface with the operator O. The remote control apparatus 100 is an apparatus that allows the operator O to operate medical equipment held by the surgical manipulators 201. Specifically, the remote control apparatus 100 is configured to transmit action mode instructions which are inputted by the operator O and are to be executed by the instruments 201a and endoscope 201b, to the patient-side system 200 through the controller 206. The remote control apparatus 100 is installed beside the operation table 300 so that the operator O can see the state of the patient P very well while operating operation handles 1, for example. The remote control apparatus 100 may be configured to transmit the action mode instructions wirelessly and installed in a room different from the operation room where the operation table 300 is installed.

The action modes to be executed by the instruments 201a include a mode of actions to be taken by each instrument 201a (a series of positions and postures) and actions to be executed by the function of each instrument 201a. For the instrument 201a which is a pair of grasping forceps, for example, the action mode to be executed by the instrument 201a includes roll and pitch positions of the wrist of the end effector and the action to open or close the jaws. For the instrument 201a which is a high-frequency knife, the action mode to be executed by the instrument 201a includes vibration of the high-frequency knife, specifically, supply of current to the high-frequency knife. For the instrument 201a which is a snare wire, the action mode to be executed by the instrument 201a includes a capturing action and an action to release the captured object and moreover includes an action to supply current to a bipolar or monopolar instrument to burn off the surgery site.

The action mode to be executed by the endoscope 201b includes the position and posture of the tip of the endoscope 201b or setting of the zoom magnification, for example.

As illustrated in FIG. 1, the remote control apparatus 100 is provided with a cover 101. The cover 101 covers the right and left sides of the remote control apparatus 100 (on X1 and X2 sides), the back side (on Y2 side), and the top side (on the Z1 side). FIGS. 2 to 11 illustrate the remote control apparatus 100 with the cover 101 removed for convenience.

Figure 2:
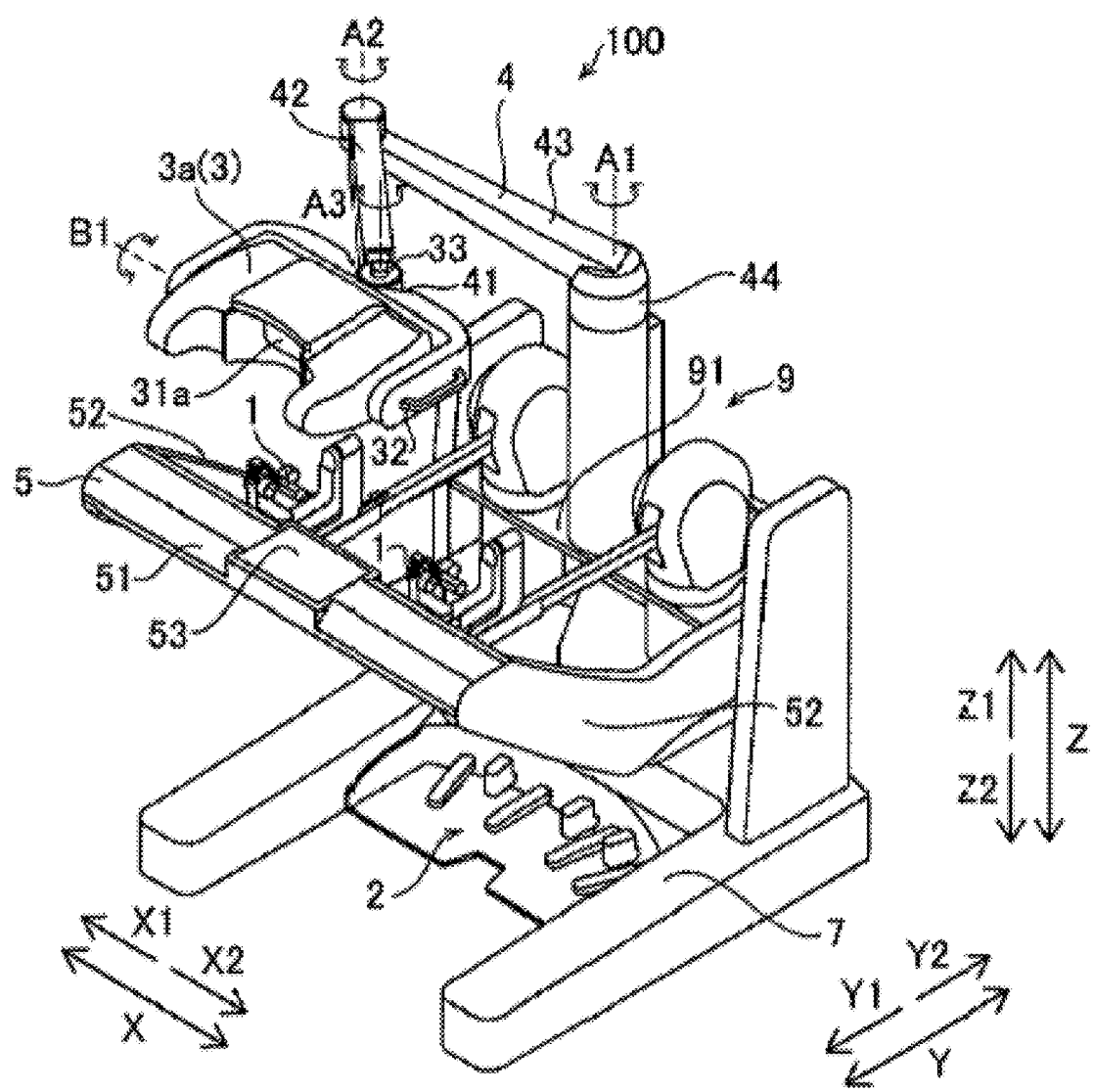
FIG. 2 is a view of the remote control apparatus according to a first embodiment with the scope type display mounted thereon.
Figure 4:
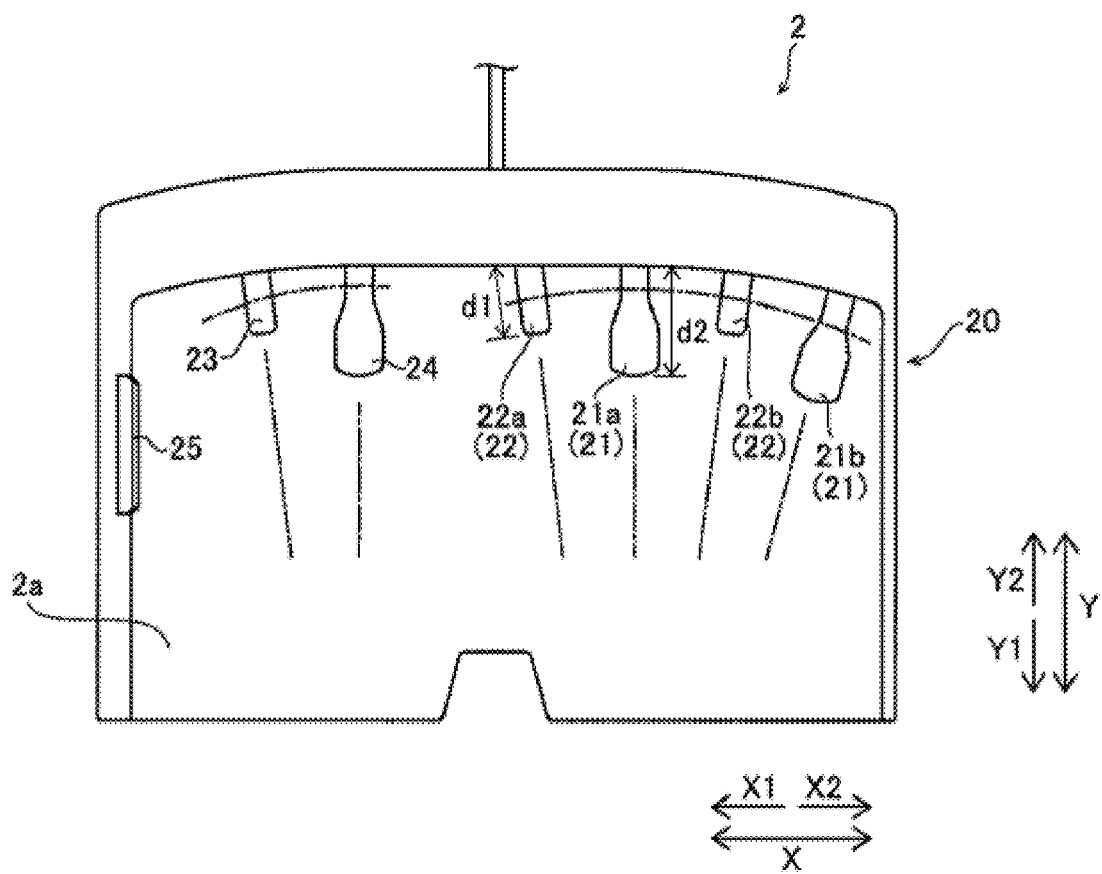
FIG. 4 is a plan view illustrating an operation pedal section of the remote control apparatus.

As illustrated in FIGS. 2 and 4, the remote control apparatus 100 includes operation handles 1, an operation pedal section 2, a display supporting arm 4 supporting a display 3, an armrest 5 supporting the arms of the operator O, and a control apparatus 6, and a base 7. The remote control apparatus 100 further includes a positioning section 8 and a supporting mechanism 9. The supporting mechanism 9 supports the operation handles 1 and armrest 5.

The operation handles 1 are provided in order to remotely operate medical equipment held by the surgical manipulators 201. Specifically, the operation handles 1 accept operations by the operator O for operating medical equipment (the instruments 201a and endoscope 201b). The operation handles 1 include a pair of operation handles 1 arranged side by side in the X direction. The right operation handle 1 (on the X2 side) of the pair of operation handles 1 is operated by the right hand of the operator O while the left operation handle 1 (on the X1 side) is operated by the left hand of the operator O.

The operation handles 1 are attached to a supporting section 91 of the supporting mechanism 9. The operation handles 1 extend from the back side (the Y2 side) of the remote operation apparatus 100 toward the front side (the Y1 side). Plural joints are provided between the supporting section 91 and each operation handle 1 so that the operation handles 1 move relative to the supporting section 91 in a predetermined three-dimensional operation range A (see FIGS. 7 and 8). Specifically, the operation handles 1 are configured so as to move relative to the supporting section 91, up and down (in the Z direction), right and left (in the X direction), and forward and backward (in the Y direction). Each joint between the supporting section 91 and operation handles 1 is provided with a not-illustrated position detector that detects the positional relationship between the joints. The position detector is an encoder, a resolver, or a potentiometer, for example. The position detector thereby detects the positions of the operation handles 1 relative to the supporting section 91.

The remote control apparatus 100 and patient-side system 200 constitute a master-slave system in terms of controlling motion of the instrument arms 201A and camera arm 201B. The operation handles 1 constitute an operating section on the master side in the master-slave system, and the instrument arms 201A grasping medical equipment and the camera arm 201B constitute an operating section on the slave side. When the operator O operates the operation handles 1, the motion of the instrument arms 201A or camera arm 201B is controlled so that the tips (the end effectors of the instruments 201a) of the instrument arms 201A and the tip (the endoscope 201b) of the camera arm 201B move following the movement of the operation handles 1.

The patient-side system 200 controls the motion of the instrument arms 201A in accordance with the set motion scaling ratio. When the motion scaling ratio is set to ½, for example, the end effectors of the instruments 201a move ½ of the movement distance of the operation handles 1. This allows for precise fine surgery. The operation handles 1 are attached to the base 7 and extend toward the operator O in the Y direction.

Figure 5:
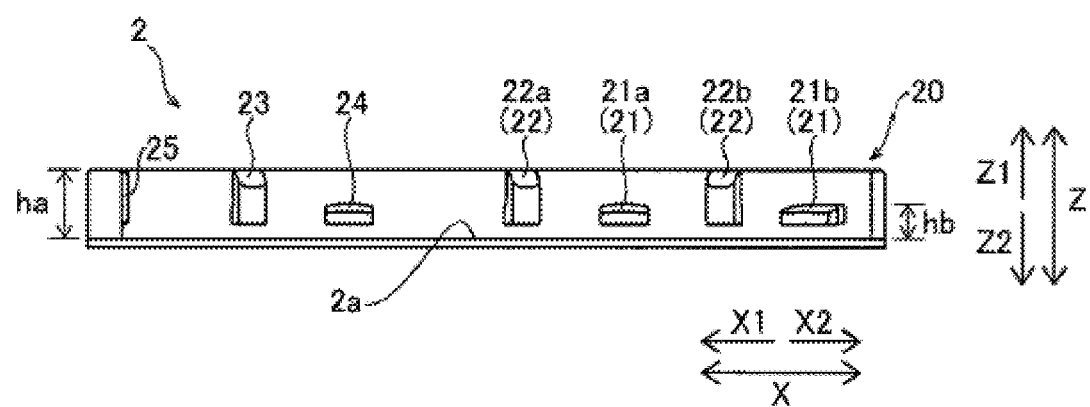
FIG. 5 is a front view illustrating the operation pedal section of the remote control apparatus.

The operation pedal section 2 includes plural pedals 20 to execute functions concerning surgical equipment as illustrated in FIGS. 4 and 5. The pedals 20 are arranged on a base 2a. The pedals 20 include coagulation pedals 21, cutting pedals 22, a camera pedal 23, a clutch pedal 24, and a side pedal 25. The coagulation pedals 21, cutting pedals 22, camera pedal 23, and clutch pedal 24 are pressed down for operation. The side pedal 25 is pressed in a horizontal direction for operation. The pedals 20 accept operations when they are pressed by about 10 mm. The force necessary to press the pedals 20 is set according to the standards so that the pedals 20 can be operated with force as small as possible.

The coagulation pedals 21 enable surgical equipment to coagulate surgery sites. Specifically, when the coagulation pedals 21 are operated, voltage for coagulation is applied to the instruments 201a to coagulate surgery sites. The coagulation pedals 21 include coagulation pedals 21a and 21b. The coagulation pedal 21a is located to the left (on the X1 side) of the coagulation pedal 21b. The coagulation pedal 21a is used in relation to the instrument 201a of the instrument arm 201A controlled by the left operation handle 1, for example. The coagulation pedal 21b is used in relation to the instrument 201a of the instrument arm 201A controlled by the right operation handle 1, for example.

The cutting pedals 22 enable surgical equipment to cut surgery sites. Specifically, when the cutting pedals 22 are operated, voltage for cutting is applied to the instruments 201a to cut surgery sites. The cutting pedals 22 include cutting pedals 22a and 22b. The cutting pedal 22a is located to the left (on the X1 side) of the cutting pedal 22b. The cutting pedal 22a is used in relation to the instrument 201a of the instrument arm 201A controlled by the left operation handle 1, for example. The cutting pedal 22b is used in relation to the instrument 201a of the instrument arm 201A controlled by the right operation handle 1, for example.

The camera pedal 23 is used to control the position and orientation of the endoscope 201 that captures images within the body cavity. Specifically, the camera pedal 23 enables control of the endoscope 201b by the operation handles 1. The position and orientation of the endoscope 201b are controllable by the operation handles 1 while the camera pedal 23 is being pressed. The endoscope 201b is controlled by using both of the right and left operation handles 1, for example. Specifically, when the operator O rotates the right and left operation handles 1 about the middle point between the right and left operation handles 1, the endoscope 201b is rotated. When the operator O presses the right and left operation handles 1 together, the endoscope 201b goes further into the body cavity. When the operator O pulls the right and left operation handles 1 together, the endoscope 201b retracts. When the operator O moves the right and left operation handles 1 together up, down, right, and left, the endoscope 201b moves up, down, right, and left, respectively.

The clutch pedal 24 is used to temporarily disconnect control-related connection between the operation handles 1 and the surgical manipulators 201 to stop movement of the surgical equipment. Specifically, while the clutch pedal 24 is being operated, the surgical manipulators 201 of the patient-side system 200 do not work even if the operation handles 1 are operated. For example, when the operation handles 1 are operated and moved to the edge of the movement range thereof, the operator O operates the clutch pedal 24 to temporarily disconnect the control-related connection and then returns the operation handles 1 to the center of the operation range. When the operator O stops operating the clutch pedal 24, the operation handles 1 are again connected to the surgical manipulators 201. The operator O restarts the operation for the operation handles 1 from the center thereof.

The side pedal 25 is used to change the instrument arms 201A controlled by the operation handles 1. The surgical manipulators 201 include four surgical manipulators 201, for example. Operation of the side pedal 25 changes which of the three instrument arms 201A, other than the camera arm 201B, is being controlled by the right or left handle 1. The side pedal 25 is pressed leftward (in the X1 direction) for operation. For example, operation of the side pedal 25 changes which of the instrument arms 201A is being controlled by the right operation handle 1. In other words, the instrument arm 201A being controlled by the right operation handle 1 is changed but the instrument arm 201A being controlled by the left operation handle 1 is not changed.

As illustrated in FIGS. 4 and 5, the pedals 20 are arranged from left (the X1 side) to right (the X2 side) sequentially in the following order: the side pedal 25, camera pedal 23, clutch pedal 24, cutting pedal 22a, coagulation pedal 21a, cutting pedal 22b, and coagulation pedal 21a.

The coagulation pedals 21 and cutting pedals 22 are alternately disposed in the horizontal direction. Pairs of coagulation pedals 21 and cutting pedals 22 are thereby operated in relation to the respective instruments 201a, which are controlled by the right and left operation handles 1. The coagulation pedals 21 and cutting pedals 22 are arranged on one side (the right side) of the centerline.

The pedal arrangement illustrated in FIG. 4 is suitable for operating the pairs of coagulation pedals 21 and cutting pedals 22 assigned to the respective right and left operation handles 1 with only the right foot. The pedals arrangement may be as follows: the pair of coagulation pedal 21a and cutting pedal 22a is located to the left (the X1 side) of the cameral pedal 23 and clutch pedal 24, and the cameral pedal 23 and clutch pedal 24 are located at the center (between the pair of coagulation pedal 21a and cutting pedal 22a and the pair of coagulation pedal 21b and cutting pedal 22b). This arrangement is suitable for operating the coagulation pedal 21a and cutting pedal 22a assigned to the left operation handle 1 with the left foot while operating the coagulation pedal 21b and cutting pedal 22b assigned to the right operation handle 1 with the right foot.

In the operation pedal section 2 according to a first embodiment, the pedals 20, which are pressed down for operation, are arranged at locations not overlapping each other in a planar view but overlapping each other in height. In contrast to the case where pedals are arranged in upper and lower two rows, the operator does not need to greatly move up and down his/her foot for operation. The operator O is able to operate the pedals 20 including the coagulation pedals 21 and cutting pedals 22 using his/her toe with the heel on the base 2a. The operability of the pedals 20 is therefore improved while enabling a desirable number of types of input operations.

Specifically, the coagulation pedals 21, cutting pedals 22, camera pedal 23, and clutch pedal 24 are arranged at the locations not overlapping each other in the planar view but overlapping each other in height in a side view.

The side pedal 25 is also preferably arranged so as to be operated by the foot with the heal on the base 2. It is preferable to arrange the side pedal 25 at a location not overlapping with the plural pedals to be pressed down for operation in the planar view but overlapping with the plural pedals in height in a side view.

The upper end of each pedal 20 to be pressed down for operation is positioned at a different height from that of the pedals 20 adjacent thereto. This allows the operator O to determine the types of the pedals 20 without visually confirming the pedals 20. The operator O is therefore able to operate the pedals 20 while looking at the display 3. As illustrated in FIG. 5, the upper ends of the cutting pedals 22 and camera pedal 23 are located at a distance ha from the floor surface, for example. The upper ends of the coagulation pedals 21 and clutch pedal 24 are located at a distance hb from the floor surface.

The height position of the upper ends of the cutting pedals 22 is a first height position while the height position of the upper ends of the coagulation pedals 21 is a second height position, which is different from the first height position. This prevents the operator O from confusing the cutting pedals 22 with the coagulation pedals 21. The height position of the upper ends of the cutting pedals 22 may be the second height position while the height position of the upper ends of the coagulation pedals 21 is the first height position.

Preferably, the distance ha of the first height position from the floor surface is 1.5 times or more than the distance hb of the second height position from the floor surface. The operator O is thereby able to easily distinguish the cutting pedals 22 from the coagulation pedals 21 for operation without visually confirming the same. More preferably, the distance ha of the first height position from the floor surface is substantially twice the distance hb of the second height position from the floor surface. The operator O is thereby able to distinguish the cutting pedals 22 from the coagulation pedals 21 while keeping the first height position from being excessively high.

The distance ha of the first height position from the floor surface is about 50 mm, for example. The distance hb of the second height position from the floor surface is about 25 mm, for example. The operator O is thereby able to operate the cutting pedals 22 and coagulation pedals 21 with his/her heel on the base 2a and does not need to greatly raise his/her foot. The distance ha of the first height position from the floor surface may be not less than about 10 mm and not more than 200 mm. The distance hb of the second height position from the floor surface may be not less than about 5 mm and not more than 100 mm.

As illustrated in FIG. 5, the lower ends of the plural pedals 20 are positioned at substantially the same height in the operation pedal section 2.

The upper and lower ends of the side pedal 25 can be located at any height positions. Preferably, the upper end thereof is located at a higher position while the lower end is located at a lower position because it is more preferable that the side pedal 25 has a larger area of contact. In the example illustrated in FIG. 5, the upper and lower ends of the side pedal 25 are located at the same height positions as those of the camera pedal 23.

As illustrated in FIG. 4, for example, the cutting pedals 22 and camera pedal 23 are protruded by a distance d1 in a planar view (when seen in the Z direction). The coagulation pedals 21 and clutch pedal 24 are protruded by a distance d2 in a planar view. The distance d2 is greater than the distance d1, for example. The operator O is thereby able to easily distinguish the types of the pedals 20 for operation. The protrusion distances of the pedals 20 in a planar view may be different from each other or substantially the same. In this case, the pedals 20 may be protruded by the same distance in a fan shape.

The coagulation pedals 21 and clutch pedal 24 have greater widths than those of the cutting pedals 22 and camera pedal 23 in a planar view. The operator O is thereby able to easily distinguish the types of the pedals 20 for operation. The pedals 20 having two different shapes are alternately arranged in the horizontal direction.

In the operation pedal section 2 according to a first embodiment, as illustrated in FIG. 4, the plural pedals 20 are arranged in a fan shape in a planar view (when seen in the Z direction). Specifically, in a planar view of the operation pedal section 2, some of the pedals 20 are arranged in a fan shape on one side of the centerline while some of the pedals 20 are arranged in a fan shape on the other side. In other words, the pedals 20 are arranged in a fan shape around the operator O. The operator O is thereby able to operate the pedals 20 by rotating the toe with the heel on the base 2a. This improves the operability of the pedals 20 while enabling a desirable number of types of input operations.

As illustrated in FIG. 4, for example, the camera pedal 23 and clutch pedal 24 are provided on the left side (on the X1 side). The camera pedal 23 extends forward (in the Y1 direction), slightly in the rightward direction (in the X2 direction). The clutch pedal 24 extends substantially in the front-back direction (in the Y direction). The operator O thereby easily operates the camera pedal 23 and clutch pedal 24 with the left foot.

The coagulation pedals 21 (21a and 21b) and the cutting pedals 22 (22a and 22b) are provided on the right side (on the X2 side) of the centerline. The cutting pedal 22a extends forward (in the Y1 direction), slightly in the rightward direction (in the X2 direction). The coagulation pedal 21a extends substantially in the front-back direction (in the Y direction). The cutting pedal 22b extends forward (in the Y1 direction), slightly in the leftward direction (in the X1 direction). The coagulation pedal 21b extends forward (in the Y1 direction), slightly in the leftward direction (in the X1 direction). The operator O thereby easily operates the coagulation pedals 21 (21a and 21b) and the cutting pedals 22 (22a and 22b) with the right foot.

The base 2a, on which the pedals 20 are arranged, is movable in the horizontal direction. To be specific, the base 2a is movable in the front-back direction (in the Y direction). The positions of the pedals 20 can be adjusted in accordance with the posture, physique, or favorite of the operator O.

Using FIGS. 6A to 6E, a description is given of an assignment example of the coagulation pedals 21 (21a and 21b) and cutting pedals 22 (22a and 22b) of the operation pedal section 2. The coagulation pedal 21a and cutting pedal 22a are used in pair, and the coagulation pedal 21b and cutting pedal 22b are used in pair. Herein, surgery sites can be cut and coagulated with one pair of forceps (a grasper, for example). To perform cutting and coagulation with one pair of forceps, high voltage is applied to the pair of forceps for cutting while low voltage is applied for coagulation. Cutting and coagulation of surgery sites are performed by selectively using the coagulation pedal 21a (21b) and cutting pedal 22a (22b). In some cases, a sealing device for coagulation is used dedicatedly or additionally although cutting and coagulation can be performed with a grasper or the like. This is because sealing devices often include additional functions, such as a function to automatically terminate power supply when coagulation is completed.

Figure 6A:
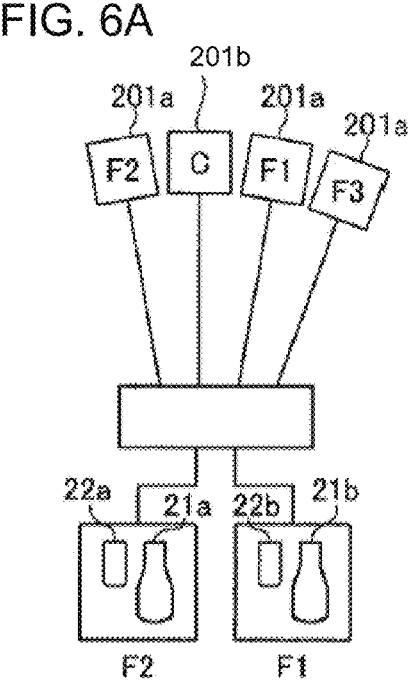
FIGS. 6A to 6E are views for explaining assignment examples of the operation pedal section of the remote control apparatus.

In the example illustrated in FIGS. 6A to 6E, a pair of bipolar forceps F1, a pair of monopolar forceps F2, and a sealing device F3 as the instruments 201a and the endoscope 201b are attached to the four surgical manipulators 201. The positional relationship between the four surgical manipulators 201 is recognized by the position detector provided for each manipulator 201. The positional relationship between the surgical manipulators 201 in the right-left direction is determined based on the positions thereof seen from the platform 203. In FIG. 6A, the pair of monopolar forceps F2 is located to the left of the camera arm 201B, to which the endoscope 201b is attached, and the pair of bipolar forceps F1 and sealing device F3 are located to the right of the camera arm 201B, in this order from left. In the assignment of the coagulation pedals 21 (21a and 21b) and cutting pedals 22 (22a and 22b), the leftmost instrument arm 201A among the instrument arms 201A to which the instruments 201a are attached is assigned to the left-side foot pedals (coagulation pedal 21a and cutting pedal 22a), and the instrument arm 201A to the right thereof is assigned to right-side foot pedals (the coagulation pedal 21b and cutting pedal 22b). Specifically, in FIG. 6A, the pair of monopolar forceps F2 is assigned to the left-side foot pedals (coagulation pedal 21a and cutting pedal 22a). The pair of bipolar forceps F1 is assigned to the right-side foot pedals (coagulation pedal 21b and cutting pedal 22b). When only two of the instrument arms 201A hold instruments 201a, the left and right instrument arms 201A are assigned to the left-side and right-side foot pedal, respectively. When only one of the instrument arms 201A holds an instrument 201a, the instrument arm 201A is assigned to the left-side foot pedals.

Figure 6B:
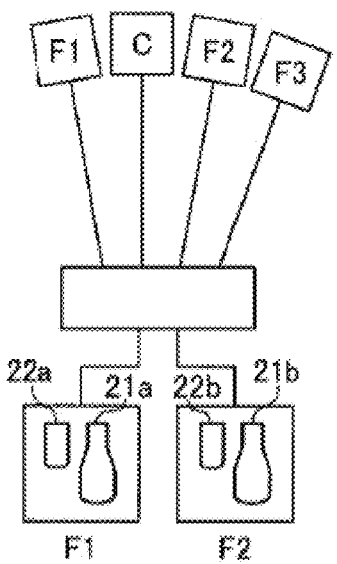

In FIG. 6B, the pair of bipolar forceps F1 and the pair of monopolar forceps F2 are replaced with each other by an assistant (a nurse, for example). In this case, the types of the instruments 201a are specified when the instruments 201a are attached to the instrument arms 201A. For example, the IC of the interface may store information including model numbers of instruments. The pair of bipolar forceps F1 is assigned to the left-side foot pedals (coagulation pedal 21a and cutting pedal 22a). The pair of monopolar forceps F2 is assigned to the right-side foot pedals (coagulation pedal 21b and cutting pedal 22b).

Figure 6C:
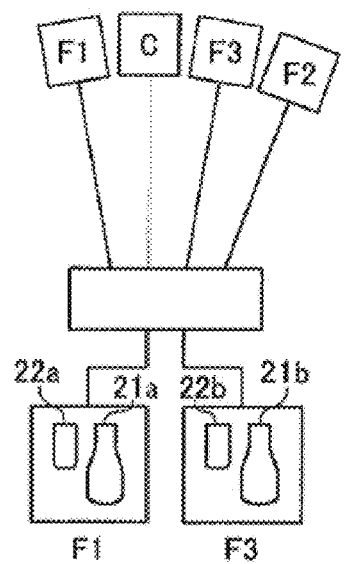

In FIG. 6C, the pair of monopolar forceps F2 and the sealing device F3 are replaced with each other by an assistant (a nurse, for example). In this case, the types of the instruments 201a are specified when the instruments 201a are attached to the instrument arms 201A. The pair of bipolar forceps F1 continues to be assigned to the left-side foot pedals (coagulation pedal 21a and cutting pedal 22a). The sealing device F3 is assigned to the right-side foot pedals (coagulation pedal 21b and cutting pedal 22b).

Figure 6D:
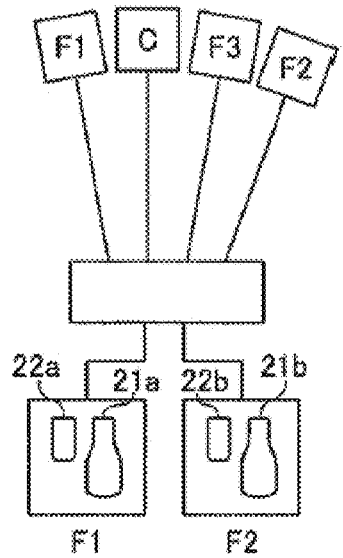

In FIG. 6D, the side pedal 25 is operated to change which of the two instrument arms 201A located on the right side 201A is being activated. Specifically, the instrument arms 201A controlled by the right operation handle 1 are switched. The instrument arm 201A to which the pair of bipolar forceps F1 is attached is controlled with the left operation handle 1 while the instrument arm 201A to which the pair of monopolar forceps F2 is attached is controlled with the right operation handle 1. The pair of bipolar forceps F1 continues to be assigned to the left-side foot pedals (coagulation pedal 21a and cutting pedal 22a). The pair of monopolar forceps F2 is assigned to the right-side foot pedals (coagulation pedal 21b and cutting pedal 22b).

Figure 6E:
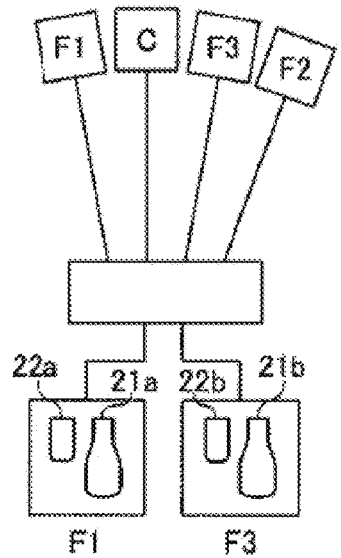

In FIG. 6E, the side pedal 25 is operated to change which of the two instrument arms 201A on the right side is being activated. Specifically, the instrument arms 201A to be controlled by the right operation handle 1 are switched. The instrument arm 201A to which the pair of bipolar forceps F1 is attached is controlled with the left operation handle 1 while the instrument arm 201A to which the sealing device F3 is attached is controlled with the right operation handle 1. The pair of bipolar forceps F1 continues to be assigned to the left-side foot pedals (coagulation pedal 21a and cutting pedal 22a). The sealing device F3 is assigned to the right-side foot pedals (coagulation pedal 21b and cutting pedal 22b).

In some cases, a simple grasper which works without electricity is used when strong grip is mainly necessary. Such instruments 201a that cannot be supplied with current are not controlled with the coagulation pedals 21 (21a and 21b) and the cutting pedals 22 (22a and 22b) and are therefore not assigned to the coagulation pedals 21 and cutting pedals 22. The assignment of the coagulation pedals 21 (21a and 21b) and cutting pedals 22 (22a and 22b) is configured so that the instrument arm 201A holding an instrument 201a that cannot be supplied with current is ignored.

The left-side foot pedals (coagulation pedal 21a and cutting pedal 22a) and right-side foot pedals (coagulation pedal 21b and cutting pedal 22b) may be assigned by another rule. For example, the instrument arms 201A to the right and left of the camera arm 201B may be always assigned to the foot pedals. For example, the one instrument arm 201A to the left of the camera arm 201B may be assigned to the left-side foot pedals (coagulation pedal 21a and cutting pedal 22a) while the left instrument arm 201A among the two instrument arms 201A located to the right of the camera arm 201B is assigned to the right-side foot pedals (coagulation pedal 21b and cutting pedal 22b).

When the instruments 201a and endoscope 201b are attached to the surgical manipulators 201 so that two of the instrument arms 201A are located to the left of the camera arm 201B, the assignment may be as follows: the left instrument arm 201A of the two instruments arm 201A located to the left of the camera arm 201B is assigned to the left-side foot pedals (coagulation pedal 21a and cutting pedal 22a) while the one instrument arm 201A located to the right of the camera arm 201B is assigned to the right-side foot pedals (coagulation pedal 21b and cutting pedal 22b). In this case, it is preferable that when it is detected that two of the instrument arms 201A are located to the left of the camera arm 201B while one of the instrument arms 201A is located to the right of the camera arm 201B, the instrument arms 201 to be switched by the side arm 25 (the target of switching by the side arm 25) are automatically set to the two instrument arms 201A located to the left of the camera arm 201B.

When plural instrument arms 201A are located on each side of the camera arm 201B, the following assignment rule is preferred. The instrument arms 201A on one side (the right side for many right-handers, for example) is set as the target of switching by the side pedal 25. The target of switching by the side pedal 25 (the instrument arms 201A to the right of the camera arm 201B or the instrument arms 201A located to the left of the camera arm 201B) may be changed by an additional control device (the touch panel (operating section 53) provided for the armrest 5, for example). Alternatively, a second side pedal (not illustrated) is further provided to the right of the coagulation pedal 21b. The side pedal 25 is operated to switch between the instrument arms 201A located to the left of the camera arm 201B while the second side pedal is operated to switch between the instrument arms 201A located to the right of the camera arm 201B.

In the examples described above, the camera arm 201B is one of the plural surgical manipulators 201 located inside. The camera arm 201B is located at the end of the surgical manipulators 201 in some cases. In such a case, the assignment is performed according to a particular rule: the leftmost instrument arm 201A is assigned to the left-side foot pedals (coagulation pedal 21a and cutting pedal 22a); the instrument arm 201A second from the left is assigned to the right-side foot pedals (coagulation pedal 21b and cutting pedal 22b); and the instrument arms 201A second and third from the left are set as the target of switching by the side pedal 25. Preferably, the target of switching by the side pedal 25 can be changed to the instrument arms 201A first and second from the left as described above.

The assignment rule may be also configured as follows: when it is detected that the camera arm 201B is one of the surgical manipulators 201 located inside, the instrument arms 201A closer to the camera arm 201B is preferentially assigned to the foot pedals. In FIG. 6A, for example, one of the instrument arms 201A is located to the left of the camera arm 201B while two are located to the right of the camera arm 201B. The instrument arm 201A located to the left of the camera arm 201B may be assigned to the left-side foot pedals (coagulation pedal 21a and cutting pedal 22a) while the instrument arm 201A closer to the camera arm 201B, among the two instrument arms 201A located to the right of the camera arm 201B may be assigned to the right-side foot pedals (coagulation pedal 21b and cutting pedal 22b). When two of the instrument arms 201A are located to the left of the camera arm 201B, one (the right one) of the two instrument arms 201A closer to the camera arm 201B is assigned to the left-side foot pedals (coagulation pedal 21a and cutting pedal 22a), and the instrument arm 201A located to the right of the camera arm 201B is assigned to the right-side foot pedals (coagulation pedal 21a and cutting pedal 22a).

In the aforementioned examples, the endoscope 201B is attached to one of the surgical manipulator 201 attached to the platform 203, and the assignment rules are set by recognizing the position of the camera arm 201B. When the camera arm 201B is provided independently of the platform 203, however, the aforementioned rule can be used by properly recognizing the positional relationship between the camera arm 201B and the instrument arms 201A with calibration in the world coordinate system. In this case, it is necessary to previously set the referential point of view used to determine the positional relationship between the surgical manipulators 201, by default or by the operator's setting.

When the surgical manipulators 201 controlled by the right and left operation handles 1 are assigned according to proper rules as described above, the two pairs of foot pedals are assigned to the plural instrument arms 201A in a simple manner without a complicated detection mechanism, such as a mechanism to detect the manipulators controlled by the right and left operation handles 1, for example.

In order for the operator O to ensure the assignment relationship between the right and left operation handles 1 and the two pairs of foot pedals for the plural instrument arms 201A, it is preferable that the assignment relationship between the operation handles 1 and foot pedals is displayed by the display 3 that displays video from the endoscope 201b as described below.

Figure 10:
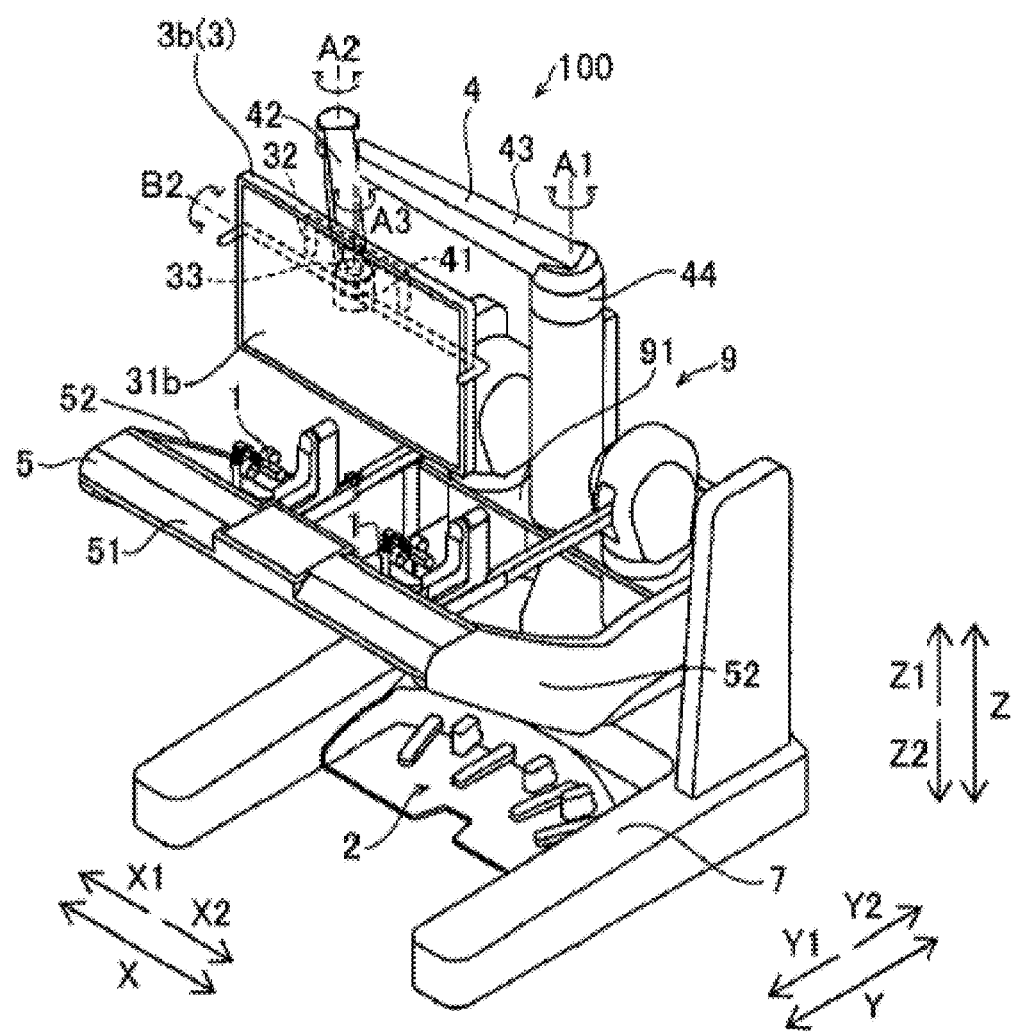
FIG. 10 is a view of the remote control apparatus with a non-scope type display mounted thereon.

The display 3 displays an image captured by the endoscope 201b. The display 3 includes a scope type display 3a or a non-scope type display 3b. The scope type display 3a is a display that the operator O looks into. The non-scope type display 3b is a concept including an open-type display that the operator O looks at without looking into and that has a flat screen, such as a normal personal computer display. The scope and non-scope type displays 3a and 3b are selectively attachable to the remote control apparatus 100. Specifically, as illustrated in FIG. 2, the scope type display 3a includes a display 31a, a grip section 32, and an attachment section 33. The non-scope type display 3b includes a display 31b, a grip section 32, and an attachment section 33 as illustrated in FIG. 10. The attachment section 33 of the scope and non-scope type display 3a or 3b is attachable to the mounting section 41 of the display supporting arm 4 of the remote control apparatus 100. In other words, the scope or non-scope type display 3a or 3b mounted on the remote control apparatus 100 is configured to be supported by the display supporting arm 4. This allows the remote control apparatus 100 to be used as either an immersive remote control apparatus or an open-type remote control apparatus. The remote control apparatus 100 is versatile in terms of the display 3.

Surgery often takes several hours. Surgeons who work for a long time with an immersive remote control apparatus sometimes experience a sense of isolation. Switching the remote control apparatus 100 to an open-type remote control apparatus before or during surgery makes surgeons more likely to have a sense of performing the surgery within a team.

The display of the remote control apparatus is versatile and expandable. If the display is broken or damaged, it is therefore only necessary to repair the display, and it is unnecessary to replace the entire apparatus. Moreover, the display can be upgraded without replacing the entire apparatus each time a higher definition or a higher quality display is developed. The operator can select a display of a favorite maker and favorite specifications (size, shape, type of operation panel, and the like).

Figure 3:
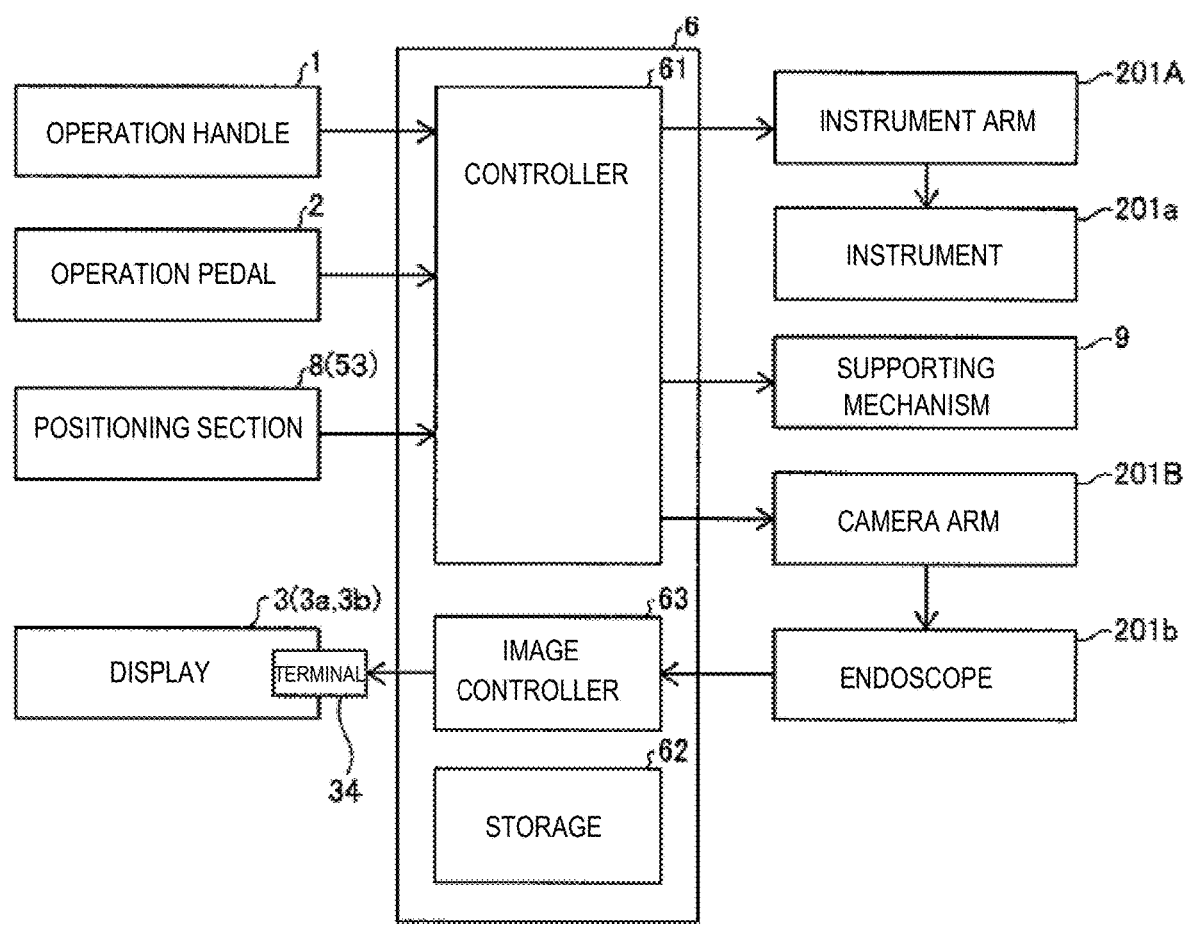
FIG. 3 is a block diagram illustrating a control-related configuration of the remote control apparatus.

The display 3 include a terminal 34 as illustrated in FIG. 3. The terminal 34 includes a terminal capable of transmitting video, such as a serial digital interface (SDI) terminal, an analogue component terminal, a high-definition multimedia interface (HDMI, registered trademark) terminal, or a universal serial bus (USB) terminal. The terminal 34 is connected to the control apparatus 6. By connecting connection wire to the terminal 34, the display 3 receives image information transmitted from the control apparatus 6. The display 3 is dismounted from the remote control apparatus 100 when the connection wire from the terminal 34 is disconnected.

When the scope type display 3a is mounted, 3D image captured by the endoscope 201b held by the camera arm 201B of the patient-side system 200 is displayed on the scope type display 3a. When the non-scope type display 3b is mounted, 3D image captured by the endoscope 201b provided to the patient-side system 200 is displayed on the non-scope type display 3b. When the non-scope type display 3b is mounted, 2D image captured by the endoscope 201b provided to the patient-side system 200 may be displayed on the non-scope type display 3b.

The scope type display 3a is a viewer that the operator O looks into. The scope type display 3a displays an image for the right eye of the operator O and an image for the left eye. The scope type display 3a is a stereoscope, for example. The display 31a includes a display for the right eye and a display for the left eye. When the operator O is looking into the display 31a, the display for the right eye cannot seen by the left eye while the display for the left cannot be seen by the right eye. The display 31a is composed of a liquid crystal display, an organic EL display, or the like. The display 31a may be a projection-type display.

The non-scope type display 3b is an open-type display that the operator O is able to see without looking into and is a direct-view-type display. The display 31b of the non-scope type display 3b includes a flat or curved screen. The display 31b can be a display with a diagonal of 10 to 90 inches, for example. Considering the balance between sufficient visibility of the surgical field and easy replacement, the display 31b preferably has a diagonal of 15 to 30 inches. The display 31b is composed of a liquid crystal display, an organic EL display, or the like. The display 31b can be a projection-type display. The non-scope type display 3b may employ a publicly-known stereoscopy in order for the operator O to stereoscopically view an image captured by the endoscope 201b, such as a method using polarization glasses or a method using active shutter glasses.

The grip section 32 is gripped when the display 3 is mounted, dismounted, or moved. The grip section 32 can be gripped with one hand. The grip section 32 has a grip, recessed, or protrusion shape. The grip section 32 is provided on a lateral side or back side of the display 3 so as not to interfere with viewing the display 31a (31b). The grip section 32 can be gripped with one hand, and the grip section 32 may include plural grip sections 32. For example, the grip sections 32 may be provided on both sides of the display 3 as illustrated in FIG. 2, for example, so that the operator O sitting in front of the display 3 can grip any grip section 32 with either right or left hand.

Figure 11A:
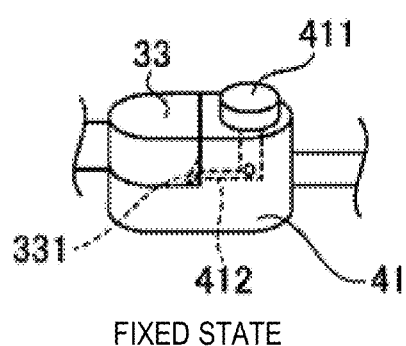
FIGS. 11A to 11C are schematic views for explaining a first example of a lock mechanism and an unlock mechanism of the remote control apparatus.
Figure 11B:
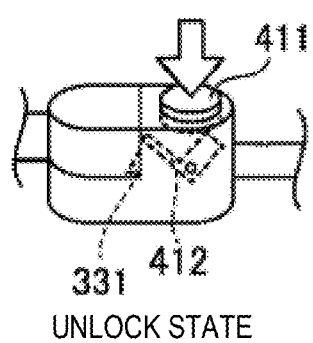
Figure 11C:
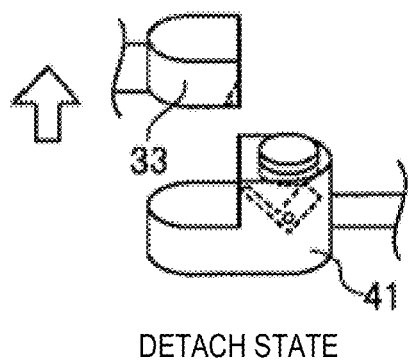

The attachment section 33 is attached to the mounting section 41 of the display supporting arm 4. The mounting section 41 is detachably attached selectively to the scope or non-scope type display 3a or 3b, for example. The attachment section 33 includes an engagement section 331 as illustrated in FIGS. 11A to 11C as a first example. The mounting section 41 includes a lock release button 411 and an engagement section 412. As illustrated in FIG. 11A, in a fixed state, the engagement section 331 of the attachment section 33 is engaged with the engagement section 412 of the mounting section 41, so that the attachment section 33 is locked with the mounting section 41 of the display supporting arm 4. The display 3 is thereby fixed and supported by the display supporting arm 4. In other words, the engagement sections 331 and 412 constitute a lock mechanism to fix the display 3 (the scope or non-scope type display 3a or 3b).

As illustrated in FIG. 11B, when the lock release button 411 is pressed down, the engagement section 412 moves and disengages from the engagement section 331. The engagement section 33 is thereby unlocked from the mounting section 41. The lock release button 411 functions as a lock release mechanism that releases the engagement by the lock mechanism composed of the engagement sections 331 and 412. The lock release mechanism is configured to release the engagement by the lock mechanism, with an action of force downward in the vertical direction. The lock release mechanism thereby easily releases the engagement by the lock mechanism.

As illustrated in FIG. 11C, the grip section 32 of the display 3 is operated upward in the vertical direction while the lock release mechanism is acting downward in the vertical direction, so that the display 3 is dismounted from the remote control apparatus 100. In such a manner, the display 3 is dismounted by performing the releasing operation downward in the vertical direction and the operation of raising the grip section upward in the vertical direction, that produce forces in the opposite directions. The display 3 is therefore dismounted stably and safely. The display 3 can be dismounted upward with space away from the display supporting arm 4, not interfering with the operation handles 1 located underneath.

Figure 12A:
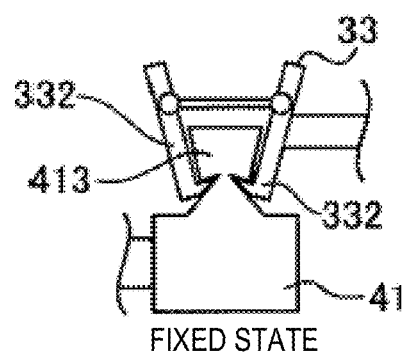
FIGS. 12A to 12C are schematic views for explaining a second example of the lock mechanism and unlock mechanism of the remote control apparatus.
Figure 12B:
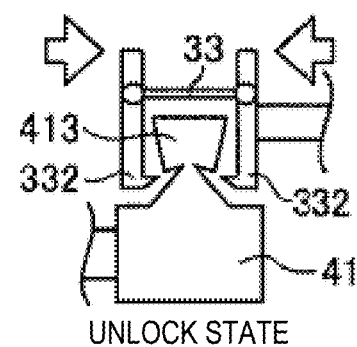
Figure 12C:
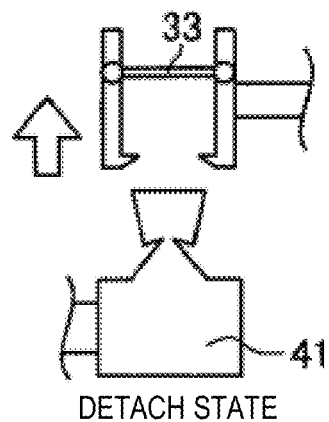

The lock mechanism and the lock release mechanism may have another configuration and may be configured as illustrated in FIGS. 12A to 12C as a second example. The attachment section 33 includes an engagement section 332 as shown in FIGS. 12A to 12C. The mounting section 41 includes an engagement section 413. As illustrated in FIG. 12A, in the fixed state, the engagement section 332 of the attachment section 33 is engaged with the engagement section 413 of the mounting section 41, so that the attachment section 33 is locked with the mounting section 41 of the display supporting arm 4. Specifically, the engagement section 332 sandwiches and grips the engagement section 413. The display 3 is thereby fixed to and supported by the display supporting arm 4. In other words, the engagement sections 332 and 413 constitute the lock mechanism to fix the display 3 (the scope or non-scope type display 3a or 3b).

As illustrated in FIG. 12B, when the engagement section 332 is pressed on both sides, the grip by the engagement section 332 is released, so that the engagement section 332 disengages from the engagement section 413. The attachment section 33 is thereby unfixed (unlocked) from the mounting section 41. As illustrated in FIG. 12C, the grip sections 32 is operated upward in the vertical direction while the attachment section 33 is unlocked. The display 3 is thereby dismounted from the remote operation apparatus 100.

Figure 13A:
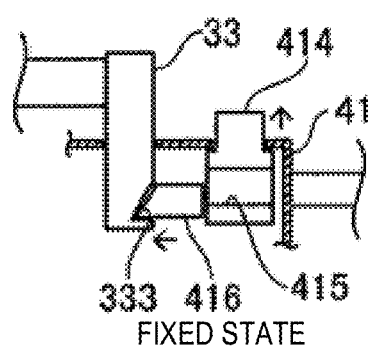
FIGS. 13A to 13C are schematic views for explaining a third example of the lock mechanism and unlock mechanism of the remote control apparatus.
Figure 13B:
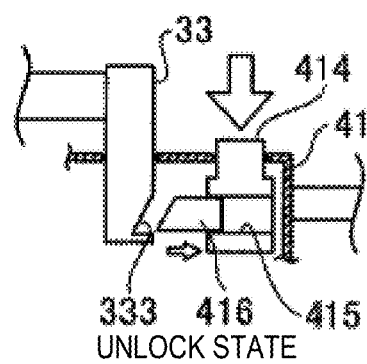
Figure 13C:
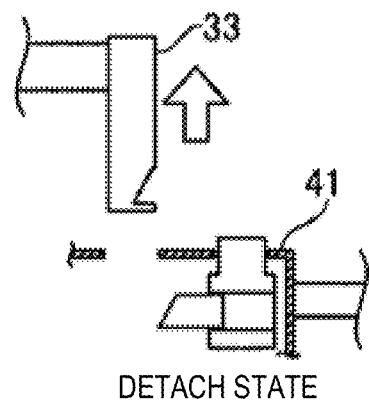

The lock mechanism and the lock release mechanism may have still another configuration as illustrated in FIGS. 13A to 13C as a third example, for example. The attachment section 33 includes a notch 333 as shown in FIGS. 13A to 13C. The mounting section 41 includes a lock release button 414, a fitting section 415, and an engagement section 416. As illustrated in FIG. 13A, the lock release button 414 is energized upward in the vertical direction by a spring or the like. The engagement section 416 is energized in a horizontal direction away from the fitting section 415. The vertical movement of the lock release button 414 and the horizontal movement of the engagement section 416 work in conjunction with a gear and the like.

In the fixed state, the notch 333 of the attachment section 33 is engaged with the engagement section 416 of the mounting section 41, so that the attachment section 33 is locked with the mounting section 41 of the display supporting arm 4. The display 3 is thereby fixed to and supported by the display supporting arm 4. In other words, the notch 333 and engagement section 416 constitute the lock mechanism to fix the display 3 (the scope or non-scope type display 3a or 3b).

As illustrated in FIG. 13B, when the lock release button 414 is pressed down, the fitting section 415 moves downward. The engagement section 416 then moves toward the fitting section 415 and fits into the fitting section 415. The notch 333 thereby disengages from the engagement section 416. The attachment section 33 is then unlocked from the mounting section 41. In other words, the lock release button 414 functions as the lock mechanism to release the engagement by the lock mechanism composed of the notch 333 and engagement section 416. The lock release mechanism releases the engagement by the lock mechanism by an action of vertically downward force.

As illustrated in FIG. 13C, the grip section 32 of the display 3 is operated upward in the vertical direction while the attachment section 33 is unlocked. The display 3 is thereby dismounted from the remote operation apparatus 100.

Having a lower-side length larger than an upper-side length, the engagement section 416 has a slope. When the attachment section 33 is pressed vertically downward against the mounting section 41, the attachment section 33 comes into contact with the slope of the engagement section 416 and presses the engagement section 416 into the fitting section 415 in the horizontal direction. When the attachment section 33 moves to a predetermined position, the engagement section 416 fits into the notch 333 and is locked in the fixed state.

The display supporting arm 4 supports the display 3 as illustrated in FIG. 2. The display supporting arm 4 includes the mounting section 41 and arm sections 42 and 43. At an end of the display supporting arm 4, the mounting section 41 is provided. The other end thereof is supported by a column 44. The column 44 is fixed to a supporting section 91 of the supporting mechanism 9. The display 3 is thus supported by the supporting section 91. The mounting section 41 of the display supporting arm 4 is rotatable around rotation axes A1, A2, and A3, which extend vertically. The mounting section 41 is supported by supporting members including vertical rotation axes so that the angle thereof is adjustable with three degrees of freedom. Specifically, the arm section 43 is supported so as to rotate in a horizontal plane around the rotation axis A1 relative to the column 44. The arm section 42 is supported so as to rotate in a horizontal plane around the rotation axis A2 relative to the arm section 43. The mounting section 41 is supported so as to rotate in a horizontal plane around the rotation axis A3 relative to the arm section 42. The display 3 attached to the mounting section 41 thus moves in the horizontal direction. The display 3 can be located at a position desired by the operator O.

When the scope type display 3a is mounted on the remote control apparatus 100, as illustrated in FIG. 2, the scope type display 3a tilts about a horizontal rotation axis B1, which is substantially orthogonal to the rotation axis A3. When the non-scope type display 3b is mounted on the remote control apparatus 100, as illustrated in FIG. 10, the non-scope type display 3b tilts about a horizontal rotation axis B2, which is substantially orthogonal to the rotation axis A3. This allows for adjustment of the angles of elevation and depression of the display 3 attached to the mounting section 41. The positioning of the display supporting arm 4 may be changed manually by the operator O or others or may be changed under movement control by a driver including a motor, an encoder, and a brake.

The armrest 5 supports arms of the operator O. The armrest 5 includes an arm supporting section 51 and a pair of connecting sections 52, and an operating section 53. The arm supporting section 51 is located in front (on the Y1 side) of the operation handles 1 and is configured to support the arms of the operator O. This stabilizes the arms of the operator O, so that the operator O can stably operate the operation handles 1. Even when the end effectors need to be moved finely, the operator O performs stabilized operation with elbows and the like on the arm rest 5. The operator O feels less strain even in long surgery. The arm supporting section 51 extends in the X direction. The pair of connecting sections 52 are provided to both ends of the arm supporting section 51 so as to sandwich the arm supporting section 51 in the X direction. The connecting sections 52 support the arm supporting section 51. The connecting sections 52 extend in the Y direction. The end of each connecting section 52 on the Y1 side is connected to the arm supporting section 51. The ends of the connecting sections 52 on the Y2 side are connected to the supporting section 91 of the supporting mechanism 9. The armrest 5 is thus supported by the supporting mechanism 9. The connecting sections 52 extend upward from the back (the Y2 side) toward the front (the Y1 side). The connecting sections 52 can be therefore connected to the base 7 at the lower positions, thus stabilizing the armrest 5. The operating section 53 is able to control settings of the remote control apparatus 100. For example, the operating section 53 is able to control the positioning of the remote control apparatus 100. In this case, the operating section 53 also functions as the positioning section 8.

As illustrated in FIG. 3, the control apparatus 6 includes a controller 61, a storage 62, and an image controller 63, for example. The controller 61 includes a calculator such as a CPU. The storage 62 includes a memory, such as a ROM and a RAM. The control apparatus 6 may be composed of a single controller performing centralized control or may be composed of plural controllers that perform decentralized control in cooperation with each other. The controller 61 determines whether the action mode instruction inputted by the operation handles 1 is to be executed by the instruments 201a or to be executed by the endoscope 201b, depending on the state of the operation pedal section 2. When determining that the action mode instruction inputted by the operation handles 1 is to be executed by the instruments 201*a*, the controller 61 transmits the action mode instruction to the instrument arm 201A. The instrument arms 201A are thereby driven for control of motions of the instruments 201*a* attached to the instrument arms 201A.

When determining that the action mode instruction inputted by the operation handles 1 is to be executed by the endoscope 201*b*, the controller 61 transmits the action mode instruction to the camera arm 201B. The camera arm 201B is thereby driven for control of motions of the endoscope 201*b* attached to the camera arm 201B.

The storage 62 stores control programs corresponding to the types of the instruments 201*a*, for example. The controller 61 reads the stored control programs according to the types of the attached instruments 201*a*. The action mode instructions from the operation handles 1 and/or the operation pedal section 2 of the remote control apparatus 100 thereby causes the respective instruments 201*a* to perform proper motions.

The image controller 63 transmits an image acquired by the endoscope 201*b* to the terminal 34 of the display 3. The image controller 63 modifies the image if necessary.

Figure 7:
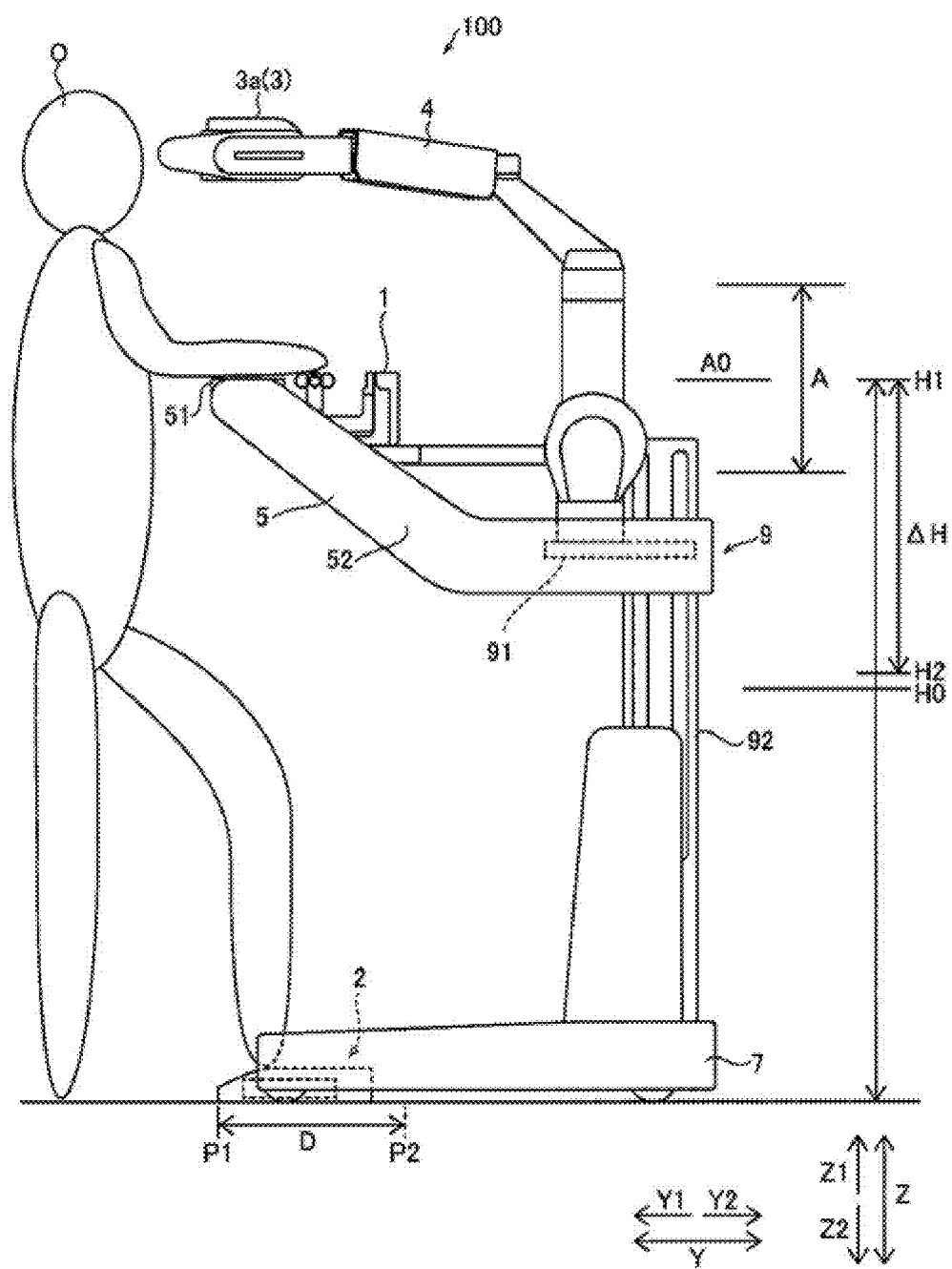
FIG. 7 is a side view illustrating a first configuration of the remote control apparatus.
Figure 8:
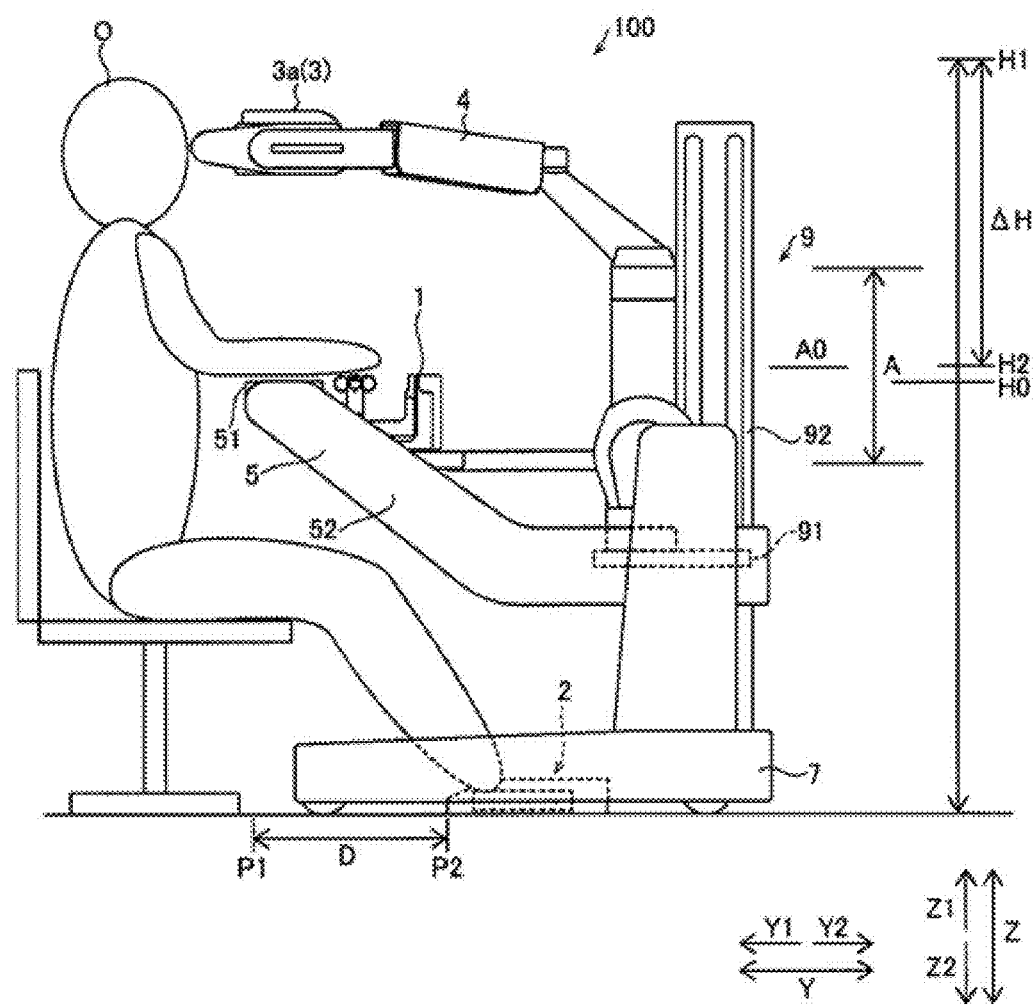
FIG. 8 is a side view illustrating a second configuration of the remote control apparatus.

In the remote control apparatus 100, as illustrated in FIGS. 7 and 8, the operation handles 1 are configured to move up and down. Specifically, the positioning section 8 accepts an operation to move the operation handles 1 up or down. Based on the operation accepted by the positioning section 8, the supporting mechanism 9 moves the operation handles 1 up or down.

The supporting mechanism 9 includes the supporting section 91 and the driver 92. The supporting section 91 supports the operation handles 1 and armrest 5. The supporting section 91 supports the display 3 through the display supporting arm 4. The driver 92 is configured to move the supporting section 91 up and down. To be specific, the driver 92 includes a motor and an encoder, for example, and moves the supporting section 91 up and down under control by the control apparatus 61. The supporting mechanism 9 may allow the operator O or others to manually change the positioning. In addition, the driver 92 of the supporting mechanism 9 may be driven pneumatically or hydraulically. The armrest 5 may be rotated relative to the supporting mechanism 9 for adjustment of the position. For example, the armrest 5 may be rotated around the rotation axis along the X direction.

The supporting mechanism 9 is configured to transition between a first mode and a second mode. In the first mode (see FIG. 7), the operation handles 1 which are positioned at a neutral position A0 of the operation range A are placed and held at a height position H1, which is 85 cm or more above the floor surface on which the remote control apparatus 100 is installed, for example. In the second mode (see FIG. 8), the operation handles 1 which are positioned at the neutral position A0 of the operation range A are placed and held at a height position H2, which is 48 cm or more below the height position H1. When the operation handles 1 which are positioned at the neutral position A0 of the operation range A, are located at the height position H1 (85 cm or more above the floor surface), the operator O is able to operate the operation handles 1 while standing up. When the operation handles 1 which are positioned at the neutral position A0 of the operation range A are located at the height position H2 (48 cm or more below the height position H1), the operator O is able to operate the operation handles 1 while sitting down. The operator O is thus able to operate the remote control apparatus 100 in a desired posture. In addition, since the operation handles 1 are supported by the supporting mechanism 9, the operator O does not need to support the operation handles 1. This prevents an increase in strain on the operator O. The armrest 5 supporting the arms of the operator O further reduces the strain on the operator O and stabilizes the arms of the operator O. The operator O is therefore able to stably operate the operation handles 1.

The supporting mechanism 9 is configured to transition between the first mode (see FIG. 7), in which the operation handles 1 are held so that the operation range A of the operation handles 1 is within a clean area set at a predetermined height position or more above the floor surface on which the remote control apparatus 100 is installed, and the second mode (see FIG. 8), in which the operation handles 1 are held so that at least a part of the operation range A of the operation handles 1 is located below the clean area.

In operation rooms, clean technique is used in order to prevent surgical incision sites and medical equipment from being contaminated by pathogen, foreign matters, or the like. In the clean technique, a clean area and a contaminated area, which is other than the clean area, are defined. The area from the floor surface to a certain height position H where foreign matters including dust and grit are more likely to remain is treated as the contaminated area in principle and is eliminated from the clean area. This area lies from the floor surface to a height position of about 70 cm, for example. The clean area is therefore set to a height position of 70 cm or more above the floor surface on which the remote control apparatus 100 is installed, for example. Members of the surgical team including the operator O make sure that only sterile objects are placed in the clean area during surgery and perform sterilization for an object which is to be moved from the contaminated area to the clean area. Similarly, when the members of the surgical team including the operator O locate their hands in the contaminated area, the members sterilize their hands before directly touching objects located in the clean area. The operation handles 1 are treated as unclean objects. Even if the operation handles 1 are located in the clean area, the operator O never accesses the patient P without sterilization or use of drape while operating the operation handles 1.

When the operation handles 1 are located so that the operation range A of the operation handles 1 is within the clean area set at the predetermined height or more above the floor surface, the operator O is able to operate the operation handles 1 while keeping his/her hands inside the clean area. If the operation handles 1 are cleaned, for example, the hands of the operator O is kept clean. When the operation handles 1 are held so that at least a part of the operation range A of the operation handles 1 is located below the clean area, the sitting operator O is able to operate the operation handles 1 at the low position. The operator O is thus able to operate the remote control apparatus 100 in a desired posture. In addition, the operation handles 1 are supported by the supporting mechanism 9, and the operator O does not need to support the operation handles 1. This can prevent an increase in strain on the operator O.

The supporting mechanism 9 is also configured to allow for transition between the first mode (see FIG. 7), in which the operation handles 1 are held at the position suitable for the operator O to operate the operation handles 1 while standing up and the second mode (see FIG. 8) in which the operation handles 1 are held at the position suitable for the operator O to operate the operation handles 1 while sitting down. When the remote operation apparatus 100 is set to the first mode, the operator O can operate the operation handles 1 while standing up. When the remote operation apparatus 100 is set to the second mode, the operator O is able to operate the operation handles 1 while sitting down. The operator O is thus able to operate the remote control apparatus 100 in a desired posture. In addition, the operation handles 1 are supported by the supporting mechanism 9, and the operator O does not need to support the operation handles 1. This can reduce an increase in strain on the operator O.

The supporting mechanism 9 is configured to move both the operation handles 1 and armrest 5 up and down at transition between the first and second modes. Specifically, the supporting mechanism 9 is configured to integrally move the operation handles 1 and armrest 5 up and down at transition between the first and second modes. This requires less components than that in the case where members for moving the operation handles 1 and armrest 5 up and down are separately provided. It is therefore possible to simplify the apparatus configuration and prevent an increase in size of the apparatus. In addition, the supporting mechanism 9 is configured to move the display 3 supported by the display supporting arm 4 up and down at transmission between the first and second modes. The supporting mechanism 9 thus integrally moves the operation handles 1, armrest 5, and display 3 up and down at transition between the first and second modes.

The supporting mechanism 9 supports the display 3 that displays an image captured by the endoscope 201b and supports the display 3 so that the position of the display 3 relative to the operation handles 1 is changeable in each of the first and second modes. To be specific, the position of the display 3 is moved relative to the operation handles 1 by the display supporting arm 4 supported by the supporting mechanism 9. The position of the display 3 relative to the operation handles 1 can be therefore changed according to the physique and posture of the operator O. This can increase the versatility of the display 3.

The positioning section 8 is configured to accept operations to move the operation handles 1, the display 3 supported by the display supporting arm 4, and the armrest 5 up and down. The positioning section 8 is also configured to accept operations to move the operation pedal sections 2 forward and backward (in the Y direction). The positioning section 8 thus accepts operations to transform the remote control apparatus 100 between first and second configurations.

In other words, the positioning section 8 is an operating section capable of receiving a configuration change instruction to change the configuration of the remote control apparatus 100 between the standing position (first configuration) and the sitting position (second configuration). The positioning section 8 includes plural operation buttons.

The supporting mechanism 9 is configured to move up and down, the operation handles 1, the display 3 supported by the display supporting arm 4, and the armrest 5. The driver 92 of the supporting mechanism 9 includes a motor and an encoder, for example. The driver 92 is driven based on instructions from the positioning section 8. The driver 92 is supported on the base 7. The driver 92 is provided near the Y2-side end of the base 7 in the Y direction (in the front-back direction) and is located at the substantially center of the base 7 in the X direction (in the right-left direction). The handles 1, the display 3 supported by the display supporting arm 4, and the armrest 5 may be independently moved up and down by the supporting mechanism 9.

In the first configuration, the supporting mechanism 9 preferably holds the operation handles 1 positioned at the neutral position A0 of the operation range A, at a height position H1 of 99 cm or more above the floor surface on which the remote control apparatus 100 is installed. In the second configuration, the supporting mechanism 9 preferably holds the operation handles 1 positioned at the neutral position A0 of the operation range A, at a height position H2, which is 50 cm or more below the height position H1.

Operation for the patient-side system 200 by the operation handles 1 is disabled at transformation between the first and second modes. To be specific, during transformation between the first and second modes, operation by the operation handles 1 is disabled, or transmission of action mode instructions is disabled. In other words, during transformation between the first and second modes, the control apparatus 61 does not transmit an action mode instruction to the patient-side system 200 even if the action mode instruction is transmitted from the operation handles 1. This prevents the patient-side system 200 from working when the operation handles 1 are operated accidentally during transformation between the first and second modes.

As illustrated in FIG. 7, when the remote control apparatus 100 is in the standing position (the first configuration), the operation handles 1 are positioned at a height suitable for the standing operator O to grip the operation handles 1 positioned at the neutral position A0 with the arms bent at substantially right angles. The display 3 is positioned at a height suitable for the standing operator O to look at the display 3. When the scope type display 3a is mounted, for example, the scope type display 3a is set at the same height as the eyes of the operator O.

When the area from the floor surface to a height position H of 70 cm is set to the contaminated area in a surgery room, the operation range A of the operation handles 1 is fully within the clean area 70 cm or more above the floor surface in the standing position mode (the first configuration) by designing based on a human model for ergonomics.

When the remote control apparatus 100 is in the standing position (the first configuration), the operation pedal section 2 is moved to a position P1 in the front side (in the Y1 side) of the remote control apparatus 100. In other words, the operation pedal section 2 is located to such a position that the standing operator O reaches the operation pedal section 2 with his/her foot while touching the operation handles 1 with his/her hands.

As illustrated in FIG. 8, when the remote control apparatus 100 is in the sitting position (the second configuration). The operation handles 1 are positioned at a height suitable for the operator O sitting in the chair to grip the operation handles 1 positioned at the neutral position A0 with his/her arms bent at substantially right angles. In addition, the display 3 is positioned at a height position suitable for the operator O sitting in the chair to look at the display 3. When the scope type display 3a is mounted, for example, the scope type display 3a is set at the same height as the eyes of the operator O. With the remote control apparatus 100, the operator O can execute surgery while sitting down in a long surgery. This can reduce fatigue of the operator O.

When the area from the floor surface to the height position H of 70 cm is set to the contaminated area in a surgery room, at least a part of the operation range A of the operation handles 1 is in the contaminated area in the sitting position mode (the second configuration) by designing based on human models for ergonomics.

When the remote control apparatus 100 is in the sitting position (the second configuration), the operation pedal section 2 is located to a position P2 in the back side (in the Y2e side) of the remote control apparatus 100. In other words, the operation pedal section 2 is located to such a position that the sitting operator O reaches the operation pedal section 2 with his/her feet while touching the operation handles 1 with his/her hands. The operation pedal section 2 is movable forward and backward by 300 mm or more (in the Y direction), for example. Preferably, the operation pedal section 2 is movable forward and backward by 350 mm or more (in the Y direction). The operation pedal section 2 can be therefore easily located to the positions suitable for the first and second configurations.

Specific dimensions and the like of the remote control apparatus 100 are designed using measurement data described in "1988 ANTHROPOMETRIC SURVEY OF U. S. ARMY PERSONNEL: METHODS AND SUMMARY STATISTICS (1988)".

The remote control apparatus 100 may be designed with reference to JIS standards. For example, "JIS Z8503-4: 2006 (ISO 11064-4: 2004), Ergonomic design of control centers, Part 4: Layout and dimensions of workstations" prescribes use of the 5th and 95th percentile human models.

The operation range A is defined as a region between 15 cm above and below the neutral position A0. The dimension of the operation range A in the height direction is defined as 30 cm. The operation range A is defined based on the dimensions of the motion range of surgical tools set to keep good operability of the surgical tools at laparoscopic surgery and the motion scaling ratio of the operation handles 1. The set motion range of the surgical tools has a dimension of 30 cm in the height direction, and the motion scaling ratio of the operation handles 1 is ½. The dimension of the operation range A in the height direction is therefore 30 cm based on the dimension of the motion range of the surgical tools in the height direction and the motion scaling ratio of the operation handles 1.

Figure 9A:
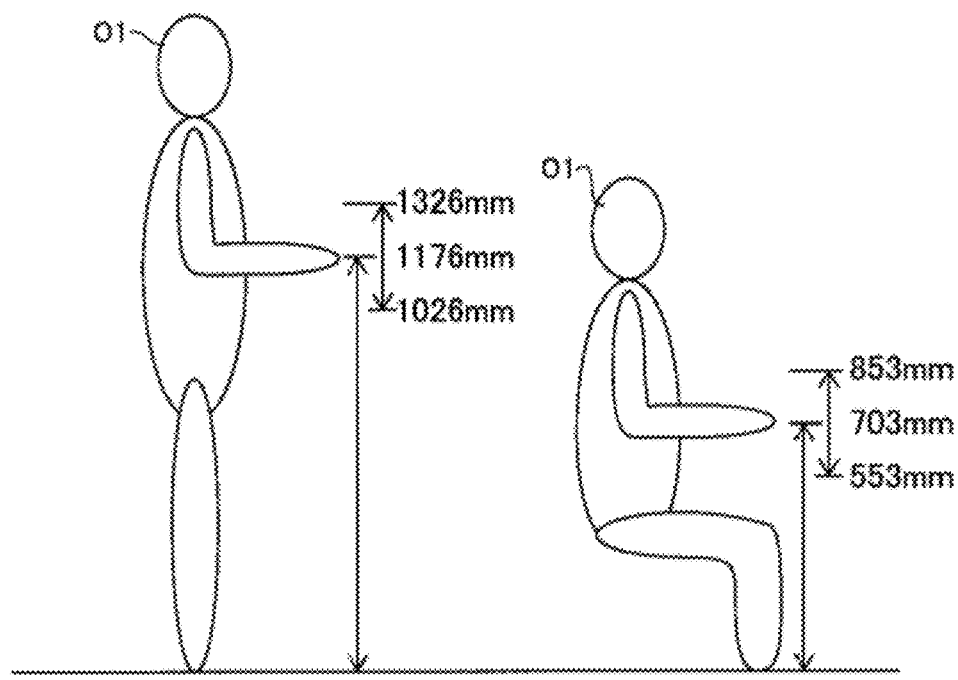
FIGS. 9A and 9B are views illustrating models of operators of the remote control apparatus.
Figure 9B:
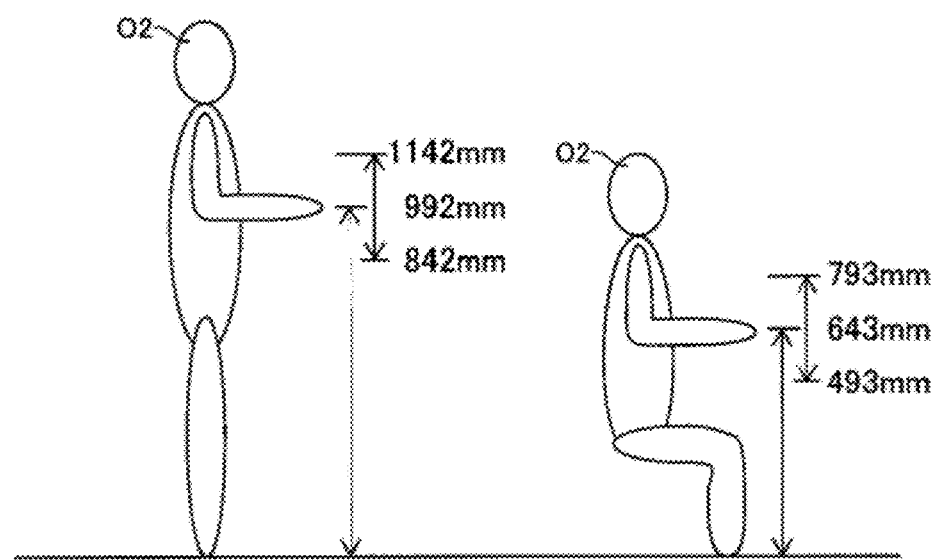

FIGS. 9A and 9B are views illustrating models of operators O, FIG. 9A illustrating a model of large operators O1, and FIG. 9B illustrating a model of small operators O2.

In FIG. 9A, the model of the large operators O1 is based on body data of German men. When the fifth largest model among 100 German male models selected at random stands and grips the operation handles 1 positioned at the neutral position A0 of the operation range A with his arms bent at right angles, the height position of the operation handles 1 is about 1176 mm, and the lower and upper limits of the height position of the operation range A are about 1026 mm and 1326 mm, respectively. On the other hand, when the fifth largest model sits down and grips the operation handles 1 positioned at the neutral position A0 of the operation range A with his arms bent at right angles, the height position of the operation handles 1 is about 703 mm, and the lower and upper limits of the height position of the operation range A are about 553 mm and about 853 mm, respectively.

In FIG. 9B, the model of the small operators O2 is based on body data of Japanese women. When the fifth smallest model among 100 Japanese female models selected at random stands and grips the operation handles 1 positioned at the neutral position A0 of the operation range A with her arms bent at right angles, the height position of the operation handles 1 is about 992 mm, and the lower and upper limits of the height position of the operation range A are about 842 mm and about 1142 mm, respectively. On the other hand, when the fifth smallest model sits down and grips the operation handles 1 positioned at the neutral position A0 of the operation range A with her arms bent at right angles, the height position of the operation handles 1 is about 643 mm, and the lower and upper limits of the height position of the operation range A are about 493 mm and about 793 mm, respectively.

Based on the aforementioned data, the height position of the operation handles 1 that allows plural operators O having different types of physique to take standing and sitting positions without any problem is as follows. First, the height position of the operation handles 1 positioned at the neutral position A0 of the operation range A in the standing position mode (the first mode) is preferably set to about 99 cm or more corresponding to the standing model of the small operators O2. This allows most operators O to comfortably operate the operation handles 1 while standing. When the operation handles 1 are configured to move down by 15 cm from the neutral position A0, the lower limit of the height position of the operation range A of the operation handles 1 in the standing position mode is 84 cm or more as described above.

The height position of the operation handles 1 positioned at the neutral position A0 in the standing position mode (the first mode) is preferably set to about 85 cm or more. When the operation handles 1 are configured to move down by 15 cm from the neutral position A0, the lower limit of the height position of the operation range A of the operation handles 1 in the standing position mode is higher than 70 cm, and the operation range A of the operation handles 1 is therefore within the clean area. Since the lower limit of the height position of the operation range A corresponding to the standing model of the small operators O2 is about 84 cm, setting the lower limit of the height position of the operation range A to 70 cm allows more operators O having different types of physiques to comfortably operate the operation handles 1 while standing up.

Next, the height position of the operation handles 1 positioned at the neutral position A0 of the operation range A in the sitting position mode (the second mode) is preferably set to about 64 cm or more corresponding to the sitting model of the small operators O2. This allows most operators O to comfortably operate the operation handles 1 while sitting down.

Next, the displacement (adjustment width) of the height position of the operation handles 1 at transition of the remote control apparatus 100 between the standing position mode and the sitting position mode is preferably set to about 35 cm or more. This is the difference between the height (about 99 cm) of the operation handles 1 positioned at the neutral position A0 corresponding to the standing model of the small operators O2 and the height (about 64 cm) of the operation handles 1 positioned at the neutral position A0 corresponding to the sitting model of the small operators O2.

In addition, the displacement of the height position of the operation handles 1 at transition of the remote control apparatus 100 between the standing position mode and the sitting position mode is preferably set to about 48 cm or more. This is the difference between the height (about 118 cm, the maximum height of the operation handles 1 positioned at the neutral position A0 in the standing position mode in this example) of the operation handles 1 positioned at the neutral position A0 corresponding to the standing model of the large operators O1 and the height (about 70 cm) of the operation handles 1 positioned at the neutral position A0 corresponding to the sitting model of the large operators O1.

As described above, the adjustment width of the height position of the operation handles 1 at transition between the standing position mode and the sitting position mode is greater than the adjustment width desirably set so as to fit to the different types of physique of the operators O in the standing position mode (about 19 cm as the difference between the height position of the operation handles 1 positioned at the neutral position A0, corresponding to the model of the large operators O1 and the height position of the operation handles 1 positioned at the neutral position A0, corresponding to the model of the small operators O2, for example) and the adjustment width desirably set so as to fit to the different types of physique of the operators O in the sitting position mode (about 6 cm as the difference between the height position of the operation handles 1 positioned at the neutral position A0 corresponding to the model of the large operators O1 and the height position of the operation handles 1 positioned at the neutral position A0 corresponding to the model of the small operators O2, for example).

If the positions of the operation handles 1 are set higher than about 118 cm (the height position of the operation handles 1 positioned at the neutral position A0 corresponding to the standing model of the large operators O1), the above-described adjustment width is further increased. It is then preferable that the adjustment width is 50 cm or more from the height position of the operation handles 1 in the standing position mode. Furthermore, the displacement of the height position of the operation handles 1 at transition of the remote control apparatus 100 between the standing position mode and the sitting position mode is preferably set to about 54 cm or more, which is the difference between the height (about 118 cm) of the operation handles 1 positioned at the neutral position A0 corresponding to the standing model of the large operators O1 and the height (about 64 cm) of the operation handles 1 positioned at the neutral position A0 corresponding to the sitting model of the small operators O2. As for definition of the operation range A, the design of the operation range A may be modified by considering the size of the operation handles 1 and the like. Although the vertical width of the operation range A is assumed to be 30 cm, the vertical width thereof may be set to 20, 25, or 35 cm, for example.

Second Embodiment

Figure 14:
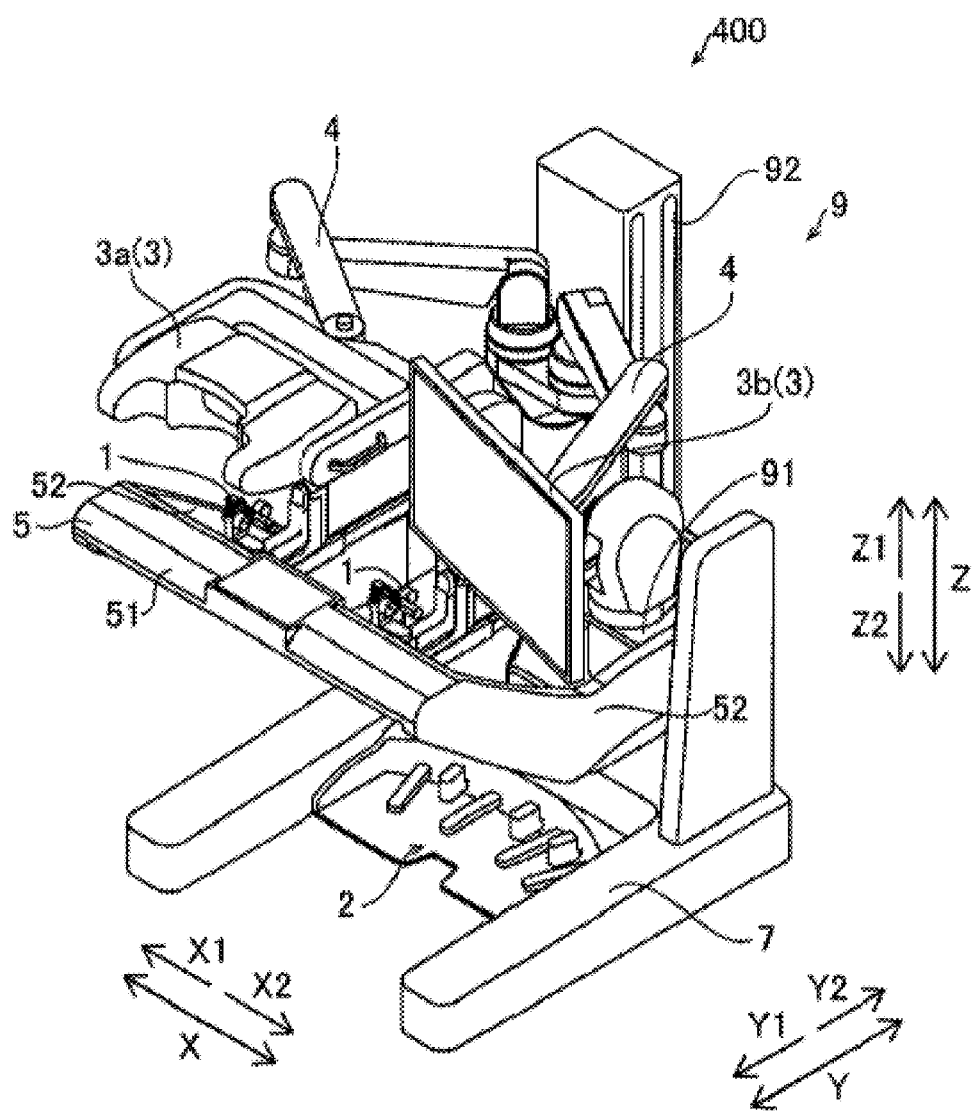
FIG. 14 is a view illustrating a remote control apparatus according to a second embodiment.

Next, with reference to FIG. 14, a second embodiment is described. In a second embodiment, description is given of an example of the configuration of a remote control apparatus including plural displays, which is different from a first embodiment in which the remote control apparatus includes one display.

As illustrated in FIG. 14, a remote control apparatus 400 according to a second embodiment includes plural displays 3. In the example illustrated in FIG. 14, both the scope type display 3*a* and non-scope type display 3*b* as the displays 3 are mounted on the remote control apparatus 400. The two displays 3 are placed right and left (side by side in the X direction).

In other words, the remote control apparatus 400 includes plural (two) mounting sections 41. Specifically, the remote control apparatus 400 includes plural (two) display supporting arms 4. The mounting sections 41 are provided at the tips of the respective display supporting arms 4. This allows both of the scope and non-scope type displays 3*a* and 3*b* to be mounted on the remote control apparatus 400, thus effectively increasing the versatility of the displays 3.

The non-scope type display 3*b*, which is one of the displays 3, displays at least one of a previously acquired image of the surgical site, information indicating the state of the surgery, and operation information. The non-scope type display 3*b* displays X-ray images or magnetic resonance images previously captured. The other scope type or non-scope type display displays a 3D image acquired from the endoscope 201*b*. This further increases the versatility and expandability such that, for example, the operator O performs surgery by mainly looking at the endoscopic image on the other display, while viewing, as needed, at least one kind of auxiliary information among the image of the surgery site previously acquired, the information indicating the state of the surgery, and the operation information.

The remote control apparatus 400 is configured so that the scope or non-scope type display 3*a* or 3*b* is selectively mounted as the main display 3. In addition, the non-scope type display 3*b* is mounted on the remote control apparatus 400 as an auxiliary display. The operator O can therefore select one of the immersive remote control apparatus and the open-type remote control apparatus and look at the auxiliary information during surgery. Since the remote control apparatus 400 is provided with plural mounting sections, it is possible to freely select on which side the main display is installed.

In the example of FIG. 14, the scope type display 3*a* and non-scope type display 3*b* are attached to the two mounting sections 41. However, the scope type display 3*a* may be attached to each of the two mounting sections 41, or the non-scope type display 3*b* may be attached to each of the two mounting sections 41.

The other configurations according to a second embodiment are the same as those of a first embodiment.

Third Embodiment

Figure 15:
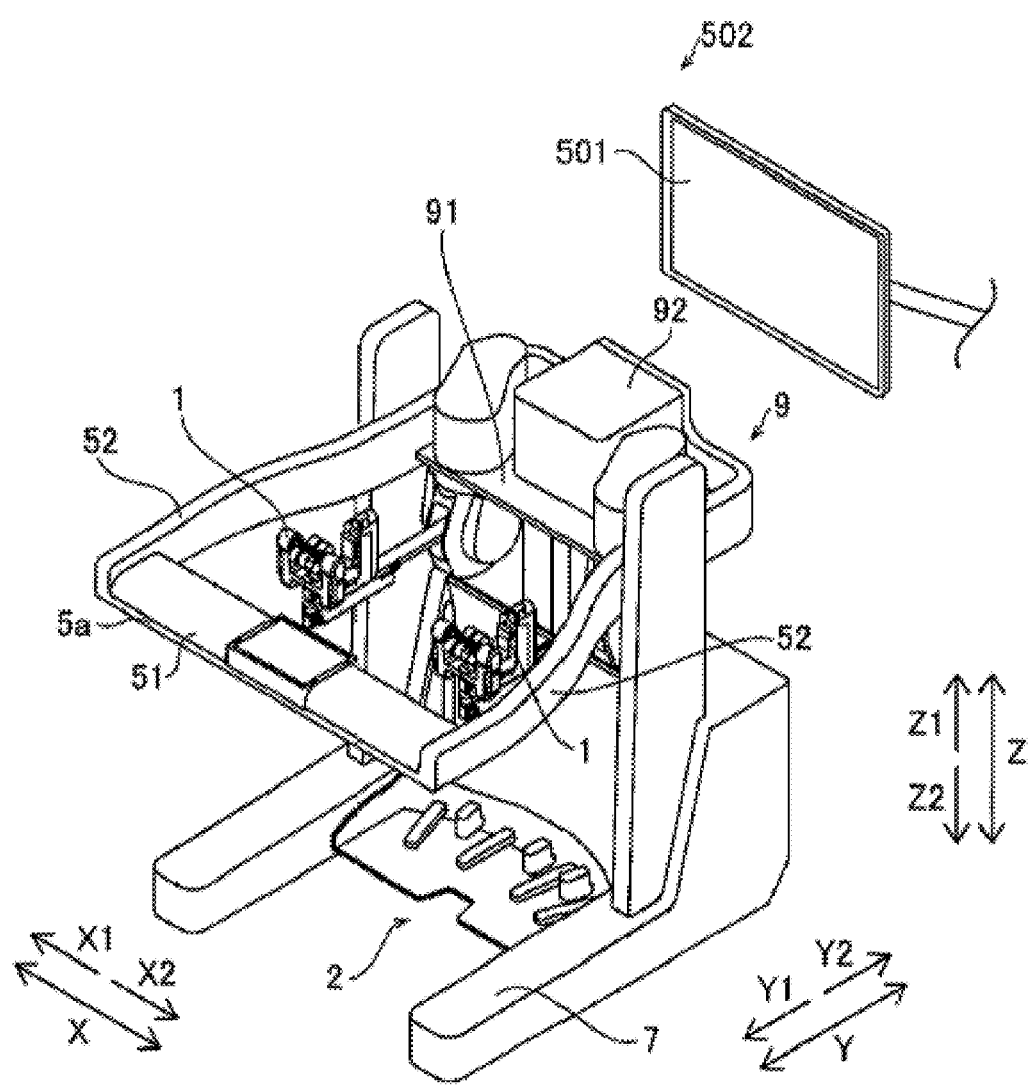
FIG. 15 is a view illustrating a remote control apparatus according to a third embodiment.

Next, with reference to FIG. 15, a third embodiment is described. In a third embodiment, description is given of a configuration example in which a display apparatus is provided separately from a remote control apparatus, which is different from first and second embodiments in which the remote control apparatus includes the display.

As illustrated in FIG. 15, a display apparatus 501 is provided separately from the remote control apparatus 500. The remote control apparatus 500 does not include a display. In addition, the remote control apparatus 500 does not include a display supporting arm supporting a display. The remote control apparatus 500 and the display apparatus 501 provided outside of the remote control apparatus 500 constitute a remote control system 502. The configuration of the remote control apparatus 500 is thereby simplified.

The display apparatus 501 is installed in back (on the Y2 side) of the remote control apparatus 500. The display apparatus 501 is placed in such a position that the operator O who is operating the remote control apparatus 500 is able to look at the screen. The display apparatus 501 includes a display apparatus such as a liquid crystal display, an organic EL display, or a plasma display and displays 2D or 3D images captured by the endoscope 201*b*. The display apparatus 501 may display at least one of a previously acquired image of the surgery site, information representing the surgery state, and operation information. The display apparatus 501 displays X-ray images or magnetic resonance images previously acquired, for example.

The other configurations according to a third embodiment are the same as those of a first embodiment.

(Modification)

It should be understood that the disclosed embodiments are shown by way of example in every respect and are not limitative. The scope of the invention is not determined by the aforementioned embodiments but is specified by Claims.

The scope of the invention includes all alternations (modifications) within meanings and scope equivalent to the scope of Claims.

In the aforementioned configuration examples of first to third embodiments, the pedals of the operation pedal section include coagulation pedals and cutting pedals. However, the invention is not limited to those configurations. For example, the pedals of the operation pedal section may include a pedal to execute a function concerning medical equipment other than the coagulation pedals and cutting pedals.

In the aforementioned examples of the first and second embodiments, the connecting sections 52 of the armrest 5 rises toward the front (the side where the operator O is located, in the Y1 direction). In the aforementioned example of the third embodiment, the connecting sections 52 of the armrest 5a extend in the horizontal direction. However, the invention is not limited to those examples. For example, as illustrated in a modification of FIG. 16, the connecting sections 52 of an armrest 5b may fall toward the front. This forms a large space at the feet of the operator O.

Figure 16:
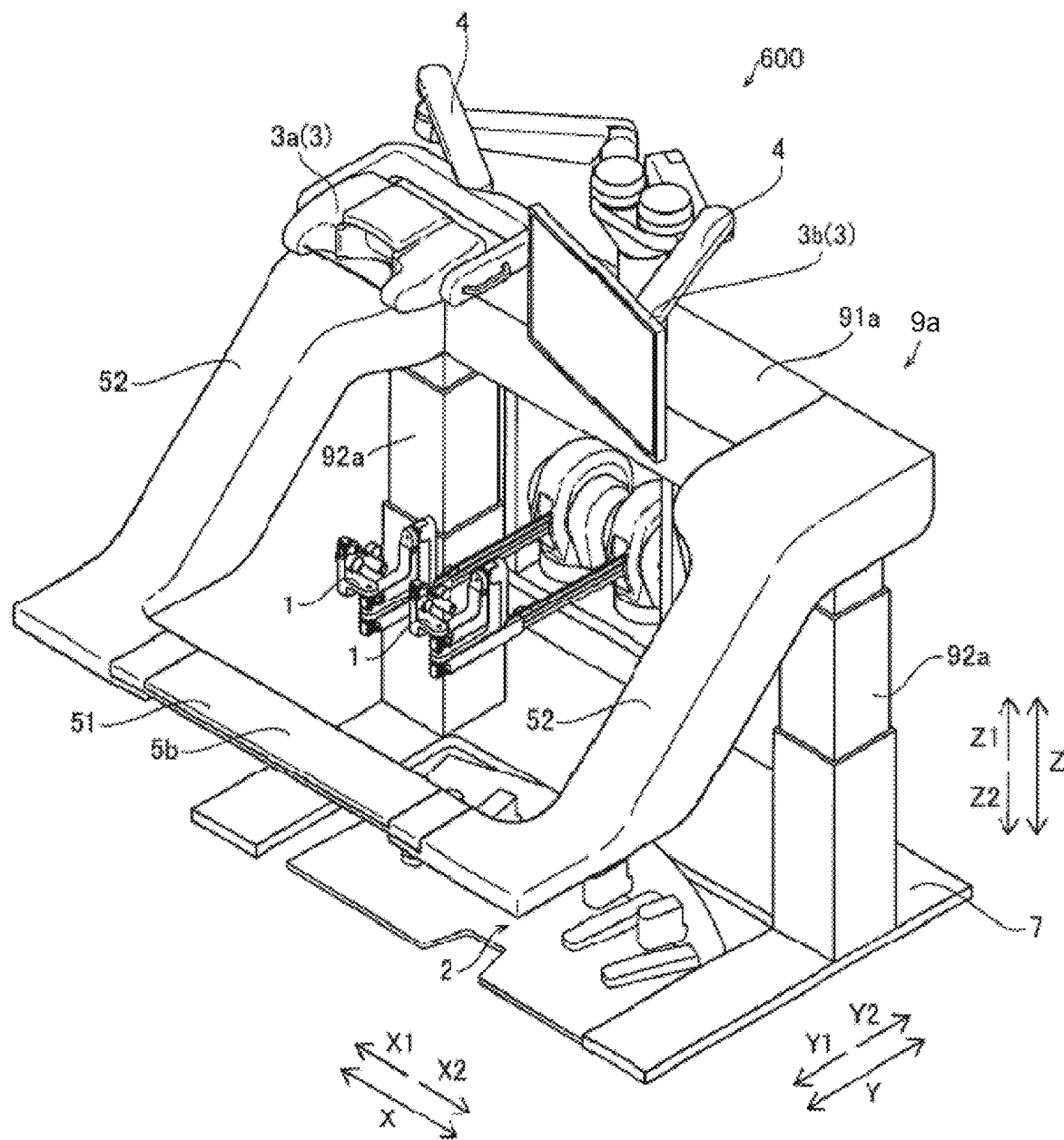
FIG. 16 is a view illustrating a remote control apparatus according to a modification of the first to third embodiments.

In the aforementioned configuration examples of the first to third embodiments, the one supporting mechanism 9 that moves the operation handles 1 and armrest 5 up and down is provided substantially at the center of the remote control apparatus in the X direction (in the right-left direction). However, the invention is not limited to those examples. For example, as illustrated in the modification of FIG. 16, a supporting mechanism 9a that supports the operation handles 1 and armrest 5 may be provided with a pair of components at both ends of a remote control apparatus 600 in the X direction (in the right-left direction). For example, the supporting mechanism 9a may include a supporting section 91a and a pair of drivers 92a. The supporting section 91a may be supported by the pair of drivers 92a arranged at the right and left ends. The pair of drivers 92a expand and contract in synchronization to move the supporting section 91a up and down.

In the aforementioned configuration examples of first to third embodiments, the operation pedal section includes seven pedals. However, the invention is not limited to these examples. For example, the operation pedal section may include not only seven pedals but also plural pedals.

In the aforementioned configuration example(s) of a first embodiment, the remote control apparatus 100 is provided with one mounting section 41 to which the display 3 is attachable. In the aforementioned configuration example(s) of a second embodiment, the remote control apparatus is provided with the two mounting sections 41 to which the display 3 is attachable. The invention is not limited to those examples. For example, the remote control apparatus may be provided with three or more mounting sections 41.

The aforementioned first to third embodiments disclose examples of the configurations in which the mounted display is connected to the remote control apparatus with a cable so as to exchange information with the same. The invention is not limited to these examples. For example, the mounted display is connected to the remote control apparatus so as to exchange information through wireless communication.

The aforementioned first to third embodiments disclose examples of the configuration in which the supporting mechanism moves the operation handles and armrest up and down. However, the invention is not limited to these examples. For example, the supporting mechanism may move the operation handles and armrest in the horizontal direction in addition to up and down movements.

The invention claimed is:

1. A remote control apparatus for remotely controlling a patient-side system including first and second medical equipment and an endoscope to capture an image of a surgery site, the remote control apparatus comprising:
    a first operation handle provided at a position to be operated by a right hand of an operator to control the first medical equipment;
    a second operation handle provided at a position to be operated by a left hand of the operator to control the second medical equipment; and
    an operation pedal section including:
        a first set of pedals for the first medical equipment including a first pedal configured to be pressed down to execute a first function concerning the first medical equipment and a second pedal configured to be pressed down to execute a second function concerning the first medical equipment;
        a second set of pedals for the second medical equipment including a third pedal configured to be pressed down to execute the first function concerning the second medical equipment and a fourth pedal configured to be pressed down to execute the second function concerning the second medical equipment;
        a third set of pedals including a fifth pedal configured to be pressed down to execute a third function different from the first and second functions and a sixth pedal configured to be pressed down to execute a fourth function different from the first, second and third functions; and
        a base on which the first set of pedals is arranged side by side on the right of the second set of pedals and the third set of pedals is arranged side by side on the left of the second set of pedals, wherein
    a distance between the second set of pedals and the third set of pedals is wider than a distance between the first set of pedals and the second set of pedals, and
    the first to sixth pedals are arranged in order from right to left on the base.

2. The remote control apparatus according to claim 1, wherein
    the first pedal and the second pedal are arranged side by side, with the first pedal arranged on the right of the second pedal,
    the third pedal and the fourth pedal are arranged side by side, with the third pedal arranged on the right of the fourth pedal,
    the fifth pedal and the sixth pedal are arranged side by side, with the fifth pedal arranged on the right of the sixth pedal,
    the first and second pedals included in the first set of pedals have different heights and different lengths from each other,
    the third and fourth pedals included in the second set of pedals have different heights and different lengths from each other, and
    the fifth and sixth pedals included in the third set of pedals have different heights and different lengths from each other.

3. The remote control apparatus according to claim 2, wherein
    the first pedal has a height lower and a length longer than those of the second pedal, the third pedal has a height lower and a length longer than those of the fourth pedal, and the fifth pedal has a height lower and a length longer than those of the sixth pedal.

4. The remote control apparatus according to claim 1, wherein
the first and second pedals have different widths from each other, the third and fourth pedals have different widths from each other, and the fifth and sixth pedals have different widths from each other.

5. The remote control apparatus according to claim 1, wherein
the fifth pedal is a camera pedal that enables the first and second operation handles to control the endoscope and the sixth pedal is a clutch pedal that temporarily disconnects a control-related connection between the first and second operation handles and the first and second medical equipment.

6. The remote control apparatus according to claim 5, wherein
the camera pedal does not have a higher height than that of the clutch pedal.

7. The remote control apparatus according to claim 1, wherein
the first pedal is a first coagulation pedal to perform an operation to coagulate the surgery site using the first medical equipment, the second pedal is a first cutting pedal to perform an operation to cut the surgery site using the first medical equipment, the third pedal is a second coagulation pedal to perform an operation to coagulate the surgery site using the second medical equipment and the fourth pedal is a second cutting pedal to perform an operation to cut the surgery site using the second medical equipment.

8. The remote control apparatus according to claim 1, wherein
the base includes a pedal arrangement region including a first region on a right side of the base and a second region on a left side of the base,
the first set of pedals and the second set of pedals are located in the first region, and
the third set of pedals is located in the second region.

9. The remote control apparatus according to claim 1, wherein
the first pedal has a thickness different from that of the second pedal, the third pedal has a thickness different from that of the fourth pedal, and the fifth pedal has a thickness different from that of the sixth pedal.

10. The remote control apparatus according to claim 1, wherein
the operation pedal section includes a seventh pedal which is configured to be operated to execute a fifth function different from the first, second, third and fourth functions, and the seventh pedal is arranged to the left of the sixth pedal.

11. The remote control apparatus according to claim 10, wherein
the patient-side system includes a third medical equipment, and
the seventh pedal is a switch pedal that changes a control target of the first operation handle from the first medical equipment to the third medical equipment.

12. The remote control apparatus according to claim 1, wherein
upper ends of the second, fourth, and sixth pedals are provided at a height 1.5 times or higher than upper ends of the first, third and fifth pedals with respect to a floor surface where the remote control apparatus is placed.

13. A remote control apparatus for remotely controlling a patient-side system including first medical equipment, second medical equipment and an endoscope to capture an image of a surgery site, the remote control apparatus comprising:
a first operation handle provided at a position to be operated by a right hand of an operator to control the first medical equipment;
a second operation handle provided at a position to be operated by a left hand of the operator to control the second medical equipment; and
an operation pedal section including:
a first set of pedals for the first medical equipment including a first pedal configured to be pressed down to execute a first function concerning the first medical equipment and a second pedal configured to be pressed down to execute a second function concerning the first medical equipment;
a second set of pedals for the second medical equipment including a third pedal configured to be pressed down to execute the first function concerning the second medical equipment and a fourth pedal configured to be pressed down to execute the second function concerning the second medical equipment;
a third set of pedals including a camera pedal that enables the first and second operation handles to control the endoscope and a clutch pedal that temporarily disconnects a control-related connection between the first and second operation handles and the first and second medical equipment; and
a base on which the first set of pedals is arranged on the right of the second set of pedals and the second set of pedals is arranged on the right of the third set of pedals, wherein
the base includes a pedal arrangement region including a first region on a right side of the base and a second region on a left side of the base,
the first set of pedals and the second set of pedals are located in the first region and the third set of pedals is located in the second region,
a distance between the second set of pedals and the third set of pedals is wider than a distance between the first set of pedals and the second set of pedals, and
the first to fourth pedals are arranged in order from right to left on the base.

14. The remote control apparatus according to claim 13, wherein
the first pedal is a first coagulation pedal to perform an operation to coagulate the surgery site using the first medical equipment; the second pedal is a first cutting pedal to perform an operation to cut the surgery site using the first medical equipment; the third pedal is a second coagulation pedal to perform an operation to coagulate the surgery site using the second medical equipment; and the fourth pedal is a second cutting pedal to perform an operation to cut the surgery site using the second medical equipment.

15. The remote control apparatus according to claim 13, wherein
the first and second pedals included in the first set of pedals are arranged side by side, the third and fourth pedals included in the second set of pedals are arranged side by side, and the camera and clutch pedals included in the third set of pedals are arranged side by side,
the first and second pedals in the first set of pedals have different heights and different lengths from each other,
the third and fourth pedals included in the second set of pedals have different heights and different lengths from each other, and the camera and clutch pedals in the third set of pedals have different heights and different lengths from each other.

16. The remote control apparatus according to claim 15, wherein
the first and third pedals have a different width from that of the second and fourth pedals.

17. The remote control apparatus according to claim 15, wherein
the first pedal has a height lower and a length longer than those of the second pedal, the third pedal has a height lower and a length longer than those of the fourth pedal, and the camera pedal has a height lower and a length longer than those of the clutch pedal.

18. The remote control apparatus according to claim 15, wherein
the first pedal has a thickness thinner than that of the second pedal, the third pedal has a thickness thinner than that of the fourth pedal, and the camera pedal has a thickness thinner than that of the clutch pedal.

19. A remote control apparatus for remotely controlling a patient-side system including a first manipulator supporting first medical equipment, a second manipulator supporting second medical equipment, and a camera arm supporting an endoscope, the remote control apparatus comprising:
a first operation handle provided at a position to be operated by a right hand of an operator to operate the first medical equipment through the first manipulator;
a second operation handle provided at a position to be operated by a left hand of the operator to operate the second medical equipment through the second manipulator; and
an operation pedal section including:
a first set of pedals including a first pedal configured to be pressed down to execute a first function concerning the first medical equipment and a second pedal configured to be pressed down to execute a second function concerning the first medical equipment;
a second set of pedals including a third pedal configured to be pressed down to execute the first function concerning the second medical equipment and a fourth pedal configured to be pressed down to execute the second function concerning the second medical equipment;
a third set of pedals including a fifth pedal configured to be pressed down to execute a third function different from the first and second functions and a sixth pedal configured to be pressed down to execute a fourth function different from the first, second and third functions; and
a base on which the first set of pedals is arranged on the right of the second set of pedals and the third set of pedals is arranged on the left of the second set of pedals, wherein
a distance between the second set of pedals and the third set of pedals is wider than a distance between the first set of pedals and the second set of pedals, and
the first to sixth pedals are arranged in order from right to left on the base.

20. The remote control apparatus according to claim 19, wherein
the first pedal included in the first set of pedals is arranged adjacent to the right of the second pedal included in the first set of pedals,
the third pedal included in the second set of pedals is arranged adjacent to the right of the fourth pedal included in the second set of pedals,
the fifth pedal included in the third set of pedals is arranged adjacent to the right of the sixth pedal included in the third set of pedals,
the first and second pedals included in the first set of pedals have different heights and different lengths from each other,
the third and fourth pedals included in the second set of pedals have different heights and different lengths from each other, and
the fifth and sixth pedals included in the third set of pedals have different heights and different lengths from each other.

21. The remote control apparatus according to claim 20, wherein
the first pedal has a height lower and a length longer than those of the second pedal, the third pedal has a height lower and a length longer than those of the fourth pedal, and the fifth pedal has a height lower and a length longer than those of the sixth pedal.

22. The remote control apparatus according to claim 20, wherein
the first pedal has a thickness thinner than that of the second pedal, the third pedal has a thickness thinner than that of the fourth pedal, and the fifth pedal has a thickness thinner than that of the sixth pedal.

23. The remote control apparatus according to claim 19, wherein
one of the fifth and sixth pedals is a camera pedal that enables the first and second operation handles to control the endoscope and the other of the fifth and sixth pedals is a clutch pedal that temporarily disconnects a control-related connection between the first and second operation handles and the first and second medical equipment.

* * * * *